(12) United States Patent
Imura et al.

(10) Patent No.: US 7,678,919 B2
(45) Date of Patent: Mar. 16, 2010

(54) METHOD FOR PRODUCING PENTACYCLIC TAXANS

(75) Inventors: Akihiro Imura, Tokyo (JP); Tatsuya Yamaguchi, Tokyo (JP); Yoshihiro Takayanagi, Tokyo (JP); Seishiro Uchida, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/238,070

(22) Filed: Sep. 25, 2008

(65) Prior Publication Data

US 2009/0030209 A1    Jan. 29, 2009

Related U.S. Application Data

(62) Division of application No. 11/579,140, filed as application No. PCT/JP2005/008034 on Apr. 27, 2005, now Pat. No. 7,456,302.

(30) Foreign Application Priority Data

Apr. 30, 2004   (JP) .............................. 2004-136359

(51) Int. Cl.
C07D 493/04   (2006.01)
(52) U.S. Cl. .................................. 546/283.7
(58) Field of Classification Search ............... 546/283.7
See application file for complete search history.

(56) References Cited

U.S. PATENT DOCUMENTS

| 6,271,408 B1 | 8/2001 | Pfander et al. |
| 2002/0143178 A1 | 10/2002 | Soga et al. |
| 2005/0070579 A1 | 3/2005 | Uchida et al. |

FOREIGN PATENT DOCUMENTS

| EP | 0 826 688 A1 | 3/1998 |
| EP | 1 221 445 A1 | 7/2002 |
| JP | 9-12578 A | 1/1997 |
| JP | 2002-332287 A | 11/2002 |
| WO | 2001-27115 A1 | 4/2001 |
| WO | 03/045953 A1 | 5/2003 |

OTHER PUBLICATIONS

Supplementary European Search Report dated Feb. 3, 2009.
Yasuyuki Takeda et al., "New Highly Active Taxoids from 9β-Dihydrobaccatin-9,10-acetals. Part 4", Bioorganic & Medicinal Chemistry, (2003), vol. 11(20), pp. 4431-4447.
M.G. Bolster et al., "The Synthesis of Ambrox-like compounds starting from (+) -larixol. Part 2", Tetrahedron (2001), vol. 57(39), pp. 8369-8379.
M.G. Bolster et al., "The Synthesis of Ambrox-like compounds starting from (+) -larixol", Tetrahedron (2001), vol. 57(26), pp. 5663-5679.
Norbert Bischofberger et al., "Synthesis of Analogues of 1,3-Dihydroxyacetone Phosphate and Clyceraldehyde 3-Phosphate for Use in Studies of Fructose-1,6-diphosphate Aldolase1", Journal of Organic Chemistry, (1988), vol. 53(15), pp. 3457-3465.

*Primary Examiner*—Patricia L Morris
(74) *Attorney, Agent, or Firm*—Sughrue Mion, PLLC

(57) ABSTRACT

Taxan derivatives are produced efficiently and inexpensively, which are useful as oral-administrable antitumor compounds.

A compound of formula (1) (wherein $R^1$ is an alkyl group, an alkenyl group, an alkynyl group, a cycloalkyl group, an aryl group or a heterocyclic group; $R^2$ is a hydroxyl group optionally having a protective group) is processed with an alkali metal permanganate to produce a compound of formula (2), which may be a starting material for oral-administrable antitumor compounds.

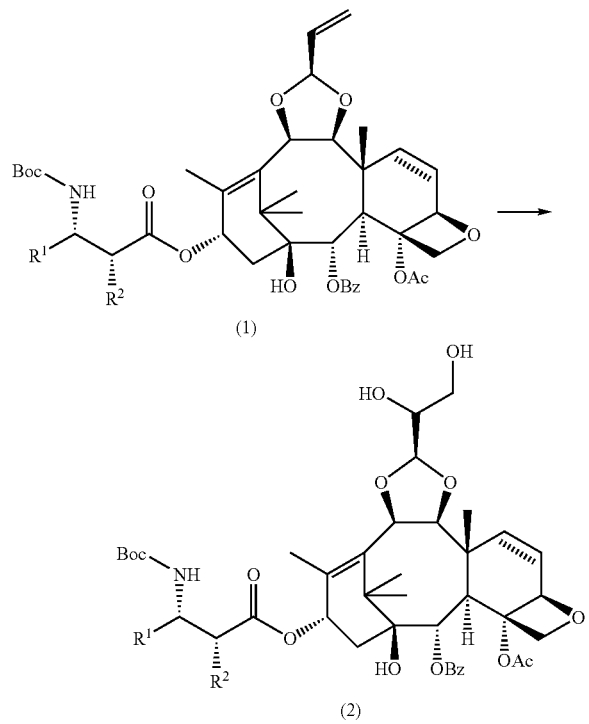

1 Claim, No Drawings

METHOD FOR PRODUCING PENTACYCLIC TAXANS

This is a divisional of application Ser. No. 11/579,140 filed Oct. 30, 2006, now U.S. Pat. No. 7,456,302 which is a National Stage Application filed under §371 of PCT Application No. PCT/JP2005/008034, filed Apr. 27, 2005. The entire disclosures of the prior application Ser. No. 11/579,140 and PCT/JP2005/008034 are incorporated herein by reference.

TECHNICAL FIELD

The present invention relates to method for producing taxan derivatives which can be orally administered and which has an antitumor activity, especially pentacyclic taxans.

BACKGROUND ART

Taxan derivatives are known as compounds having an antitumor activity (Patent References 1 to 3). Patent References 2 and 3 describe orally-administrable taxan derivatives and a method for producing such orally-administrable taxan derivatives. Patent References 2 and 3 describe a method for producing taxan derivatives where osmium tetroxide is used for the oxidation during the process (including the following Production Method 1 and Production Method 2, in which $R^1$ represents a dimethylaminomethyl group or a morpholinomethyl group, $R^2$ represents a halogen atom, or an alkoxy group having from 1 to 6 carbon atoms, $R^3$ represents a hydroxyl group optionally having a protective group).

Production Method 1:

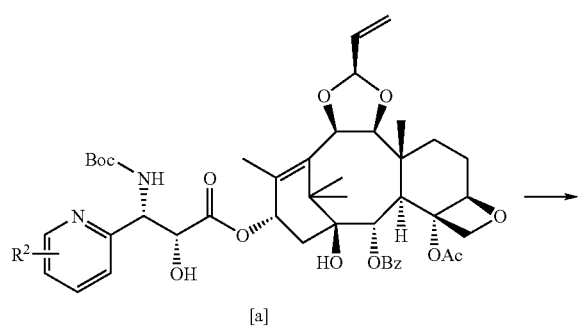

[a]

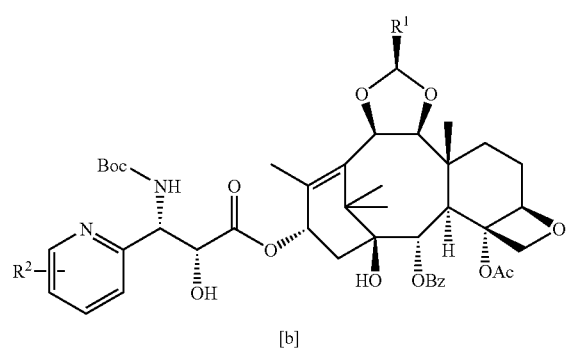

[b]

Production Method 2:

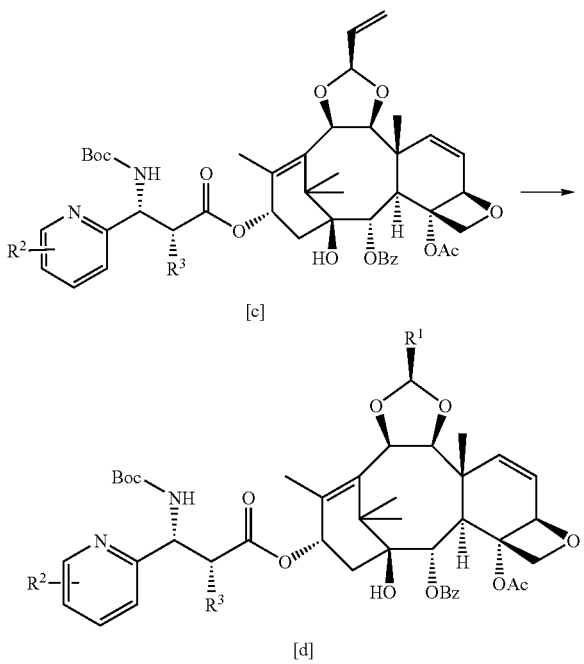

The method for producing the compound [b] from the compound [a], or the method for producing the compound [d] from the compound [c] comprises converting the terminal olefin of the compound [a] or the compound [c] into a diol by an oxidizing agent such as N-methylmorpholine-N-oxide in the presence of a catalyst of osmium tetroxide, then oxidatively cleaving them with sodium periodate or the like into an aldehyde, and reacting it with a corresponding amine to obtain the compound [b] or [d] (see Patent Reference 3, paragraphs [0058] to [0061]).

Patent Reference 1: JP-A-9-12578
Patent Reference 2: WO 01/27115
Patent Reference 3: JP-A-2002-332287

DISCLOSURE OF THE INVENTION

Problems that the Invention is to Solve

However, the above-mentioned method is extremely disadvantageous for industrial-scale production since highly-toxic osmium tetroxide is used as the catalyst and the environmental load in the method is large. In addition, the method requires multi-stage purification for removal of osmium tetroxide, and is therefore cumbersome and problematic in point of the yield.

Accordingly, an object of the present invention is to provide a method for efficiently and inexpensively producing taxan derivatives usable as orally-administrable antitumor compounds, not using osmium tetroxide but using nontoxic and inexpensive materials.

Means for Solving the Problems

The present inventors have assiduously studied, and as a result, have developed a method for obtaining taxan derivatives having a diol group, by reacting a terminal olefin-having taxan derivative with an alkali metal permanganate. Naturally it is considered that, when a compound having a complicated structure is processed with an alkali metal permanganate having a strong oxidizing capability, then it may be decomposed to lower the efficiency in industrial-scale production. According to this method, however, the terminal olefin-having taxan derivative is prevented from being decomposed and the diol group-having taxan derivative can be obtained efficiently. In addition, the present inventors have developed a method for efficiently obtaining taxan derivatives by reducing the amount of the solvent to be used for the reaction substrate. According to the method, the purification operation is easy and the purification frequency may be reduced, and therefore the loss of the product in the purification step may be reduced and the yield of the product is thereby increased. According to the method of the invention, therefore, the product can be obtained efficiently. Further, as compared with osmium tetroxide, alkali metal permanganate is inexpensive, and the method using it is therefore inexpensive and advantageous. Specifically, the invention relates to a method for producing a compound of the following general formula (2) or its salt, or their hydrate or solvate, which comprises reacting a compound of the following formula (1) with an alkali metal permanganate:

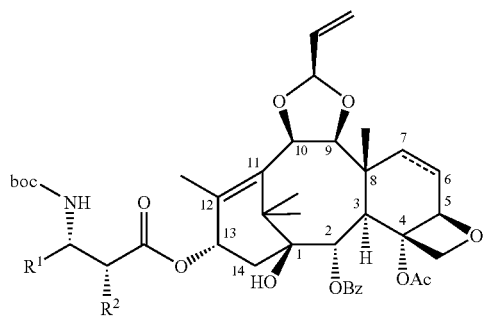

(1)

(in formula (1), the dot line part between the 6-position and the 7-position of the partial structure of the following formula (1-a):

(1-a)

means that the bond of this part may be a double bond; boc means a tert-butoxycarbonyl group; Ac means an acetyl group; Bz means a benzoyl group; $R^1$ means an alkyl group, an alkenyl group, an alkynyl group, a cycloalkyl group, an aryl group or a heterocyclic group, and the alkyl group, the alkenyl group, the alkynyl group, the cycloalkyl group, the aryl group or the heterocyclic group may be have one or more substituents selected from a group consisting of a halogen atom, a hydroxyl group, a carboxyl group, an alkyl group, an alkoxy group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group; $R^2$ means a hydroxyl group optionally having a protective group);

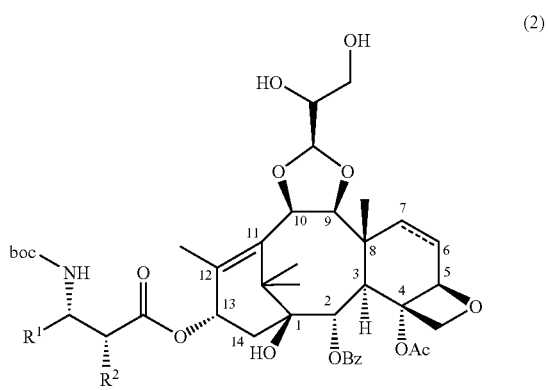

(2)

(in formula (2), $R^1$, $R^2$, boc, Ac and Bz have the same meanings as above).

The diol group of the taxan derivative of formula (2), obtained in the above production method, is converted into an intended substituent according to an ordinary known method, and further optionally, when the bond between the 6-positioned carbon and the 7-positioned carbon is a double bond, it is converted into a single bond, and/or when $R^2$ is a hydroxyl group having a protective group, the protective group is removed, whereby a taxan derivative having an antitumor effect can be obtained with ease. Specifically, the invention further relates to a method for producing a compound of the following general formula (3) or its salt, or their hydrate or solvate, which comprises;

1) a step of reacting a compound of the following general formula (1):

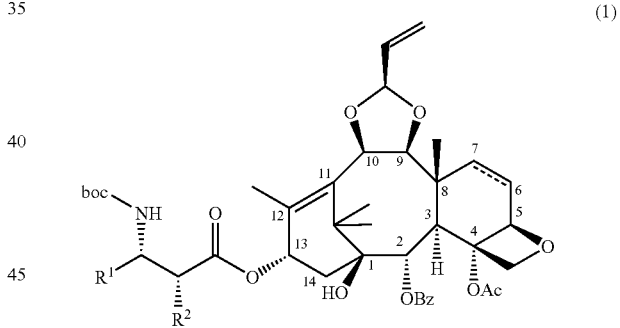

(1)

(in formula (1), the dot line part between the 6-position and the 7-position of the partial structure of the following formula (1-a):

(1-a)

means that the bond of this part may be a double bond; boc means a tert-butoxycarbonyl group; Ac means an acetyl group; Bz means a benzoyl group; $R^1$ means an alkyl group, an alkenyl group, an alkynyl group, a cycloalkyl group, an aryl group or a heterocyclic group, and the alkyl group, the alkenyl group, the alkynyl group, the cycloalkyl group, the aryl group or the heterocyclic group may be have one or more substituents selected from a group consisting of a halogen atom, a hydroxyl group, a carboxyl group, an alkyl group, an alkoxy group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group; $R^2$ means a hydroxyl group optionally having a protective group), with an alkali metal permanganate to obtain a compound of the following general formula (2):

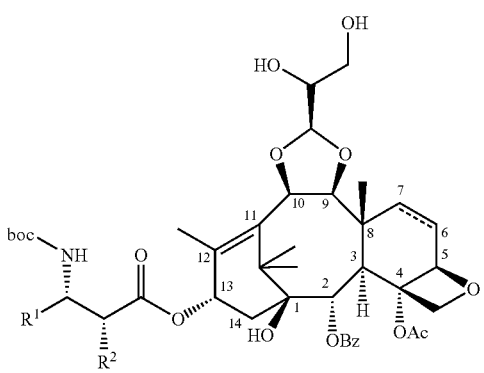

(in formula (2), $R^1$, $R^2$, boc, Ac and Bz have the same meanings as above);

2) a step of converting the group —CH(OH)CH$_2$OH in the compound of formula (2) into a group —$R^3$ {in which $R^3$ means a hydrogen atom, an alkyl group, an alkenyl group, an alkynyl group, an aryl group or a heterocyclic group, and the alkyl group, the alkenyl group, the alkynyl group, the aryl group or the heterocyclic group may have one or more substituents selected from a group consisting of an alkoxy group, an amino group, an alkylamino group, an aminoalkyl group, an alkylaminoalkyl group, a cycloalkylamino group and a nitrogen-containing, 5-membered or 6-membered saturated heterocyclic group of the following formula (3-a):

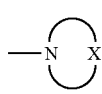

(in formula (3-a), X means an oxygen atom, a sulfur atom, CH$_2$, CH—Y, NH or N—Y; and Y means an alkyl group), (the heterocyclic group may have one or more alkyl groups on the carbon atom that constitutes the ring)};

3) when the bond between the 6-positioned carbon and the 7-positioned carbon is a double bond, a step of converting it into a single bond; and 4) when $R^2$ is a hydroxyl group having a protective group, a step of removing the protective group:

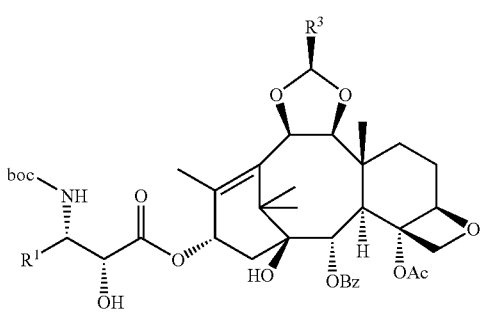

(in formula (3), $R^1$, $R^3$, boc, Ac and Bz have the same meanings as above).

In the invention, the intended taxan derivative of formula (3) is preferably a compound of the following general formula (6):

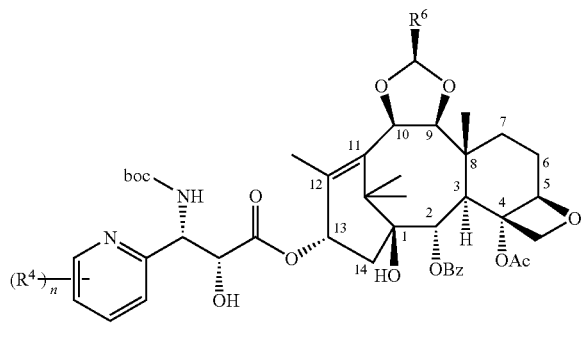

(in formula (6), boc means a tert-butoxycarbonyl group; Ac means an acetyl group; Bz means a benzoyl group; $R^4$ means a halogen atom or an alkoxy group; n indicates an integer of from 0 to 4; when n is 2 or more, then two or more $R^4$'s may be the same or different; $R^6$ means a dimethylaminomethyl group or a morpholinomethyl group). More preferably, the intended taxan derivative of formula (3) is a compound of the following general formula (11):

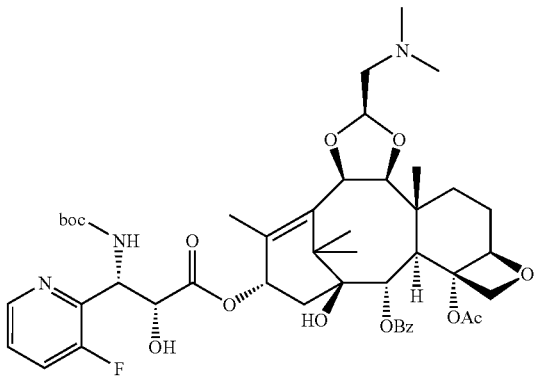

(in formula (11), boc, Ac and Bz have the same meanings as above).

Accordingly, the invention further relates to an efficient and inexpensive method for producing a taxan derivative of the following (i) to (iv), in which the product is easy to purity:

(i) A method comprising reacting a compound of the following general formula (4):

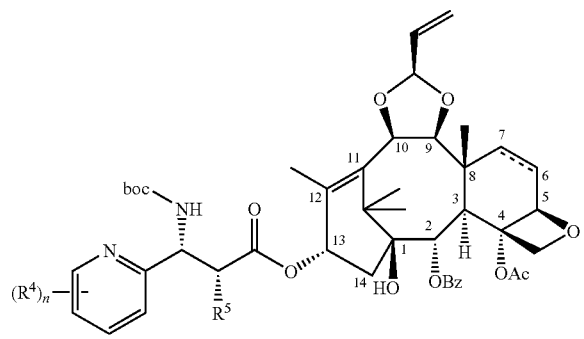

(in formula (4), the dot line part between the 6-position and the 7-position of the partial structure of the following formula (4-a):

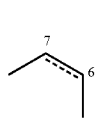

(4-a)

means that the bond of this part may be a double bond; boc means a tert-butoxycarbonyl group; Ac means an acetyl group; Bz means a benzoyl group; $R^4$ means a halogen atom or an alkoxy group; n indicates an integer of from 0 to 4; when n is 2 or more, then two or more $R^4$'s may be the same or different; $R^5$ means a hydroxyl group optionally having a protective group)

with an alkali metal permanganate in the presence of a base in at least one solvent selected from a group consisting of aqueous pyridin, aqueous tetrahydrofuran and aqueous acetone to produce a compound of the following general formula (5) or its salt, or their hydrate or solvate:

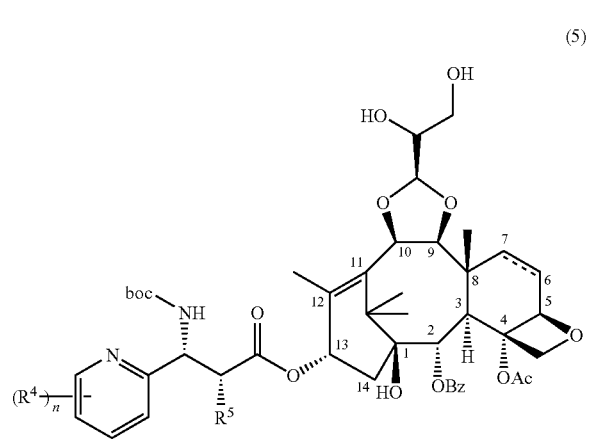

(5)

(in formula (5), $R^4$, n, $R^5$, boc, Ac and Bz have the same meanings as above).

(ii) A method for producing a compound of the following general formula (6) or its salt, or their hydrate or solvate, comprising the following steps:

1) reacting a compound of the following general formula (4):

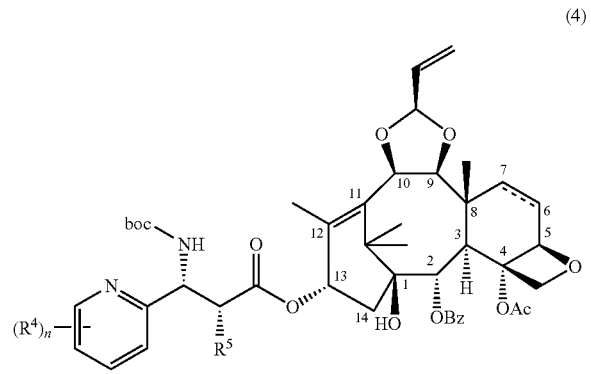

(4)

(in formula (4), the dot line part between the 6-position and the 7-position of the partial structure of the following formula (4-a):

(4-a)

means that the bond of this part may be a double bond; boc means a tert-butoxycarbonyl group; Ac means an acetyl group; Bz means a benzoyl group; $R^4$ means a halogen atom or an alkoxy group; n indicates an integer of from 0 to 4; when n is 2 or more, then two or more $R^4$'s may be the same or different; $R^5$ means a hydroxyl group optionally having a protective group)

with an alkali metal permanganate in the presence of a base in at least one solvent selected from a group consisting of aqueous pyridin, aqueous tetrahydrofuran and aqueous acetone to obtain a compound of the following general formula (5):

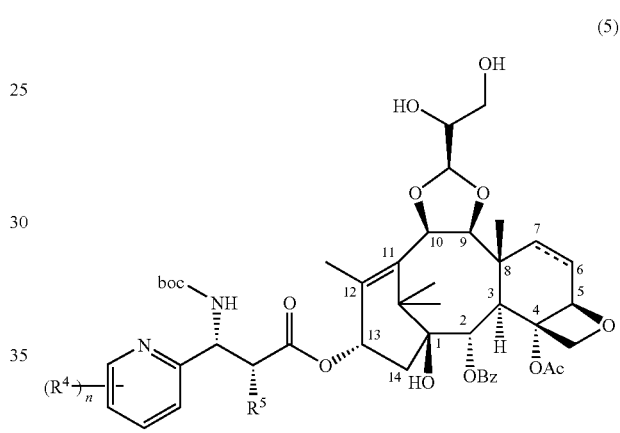

(5)

(in formula (5), $R^4$, n, $R^5$, boc, Ac and Bz have the same meanings as above), 2) a step of converting the group —CH(OH)CH$_2$OH in the compound of formula (5) into a dimethylaminomethyl group or a morpholinomethyl group;

3) when the bond between the 6-positioned carbon and the 7-positioned carbon is a double bond, a step of converting it into a single bond; and 4) when $R^5$ is a hydroxyl group having a protective group, a step of removing the protective group:

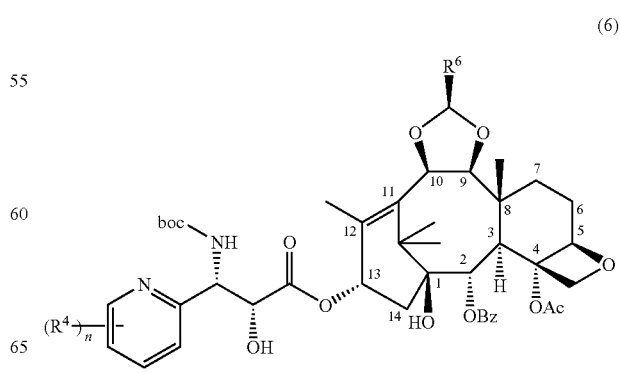

(6)

(in formula (6), $R^4$, n, boc, Ac and Bz have the same meanings as above; $R^6$ means a dimethylaminomethyl group or a morpholinomethyl group).

(iii) A method comprising reacting a compound of the following general formula (7):

(7)

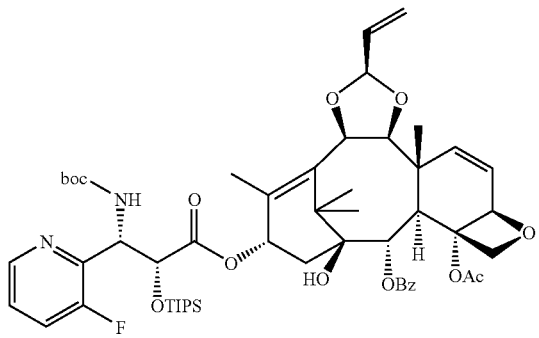

(in formula (7), boc means a tert-butoxycarbonyl group; Ac means an acetyl group; Bz means a benzoyl group; and TIPS means a triisopropylsilyl group), with potassium permanganate in aqueous pyridine, or in the presence of lithium hydroxide in aqueous pyridine to produce a compound of the following general formula (8) or its salt, or their hydrate or solvate:

(8)

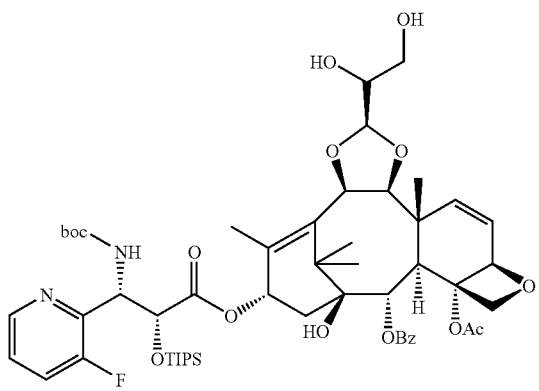

(in formula (8), boc, Ac, Bz and TIPS have the same meanings as above).

(iv) A method comprising reacting a compound of the following general formula (7):

(7)

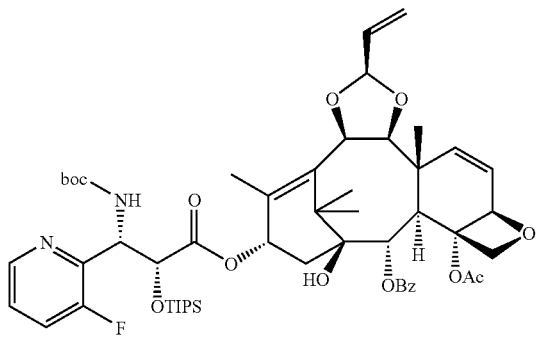

(in formula (7), boc means a tert-butoxycarbonyl group; Ac means an acetyl group; Bz means a benzoyl group; and TIPS means a triisopropylsilyl group), with potassium permanganate in aqueous pyridine, or in the presence of lithium hydroxide in aqueous pyridine to obtain a compound of the following general formula (8):

(8)

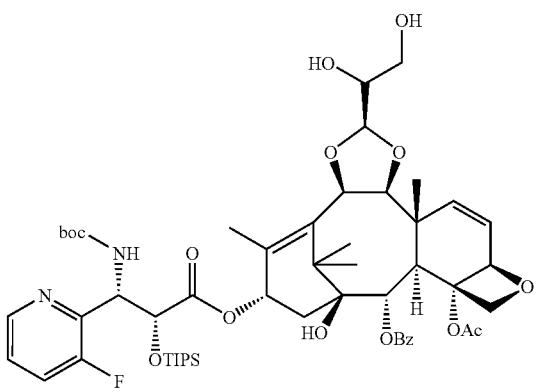

(in formula (8), boc, Ac, Bz and TIPS have the same meanings as above), then reacting the compound of formula (8) with an alkali metal periodate, and thereafter reacting it with sodium acetoxyborohydride in the presence of acetic acid and dimethylamine to obtain a compound of the following general formula (9):

(9)

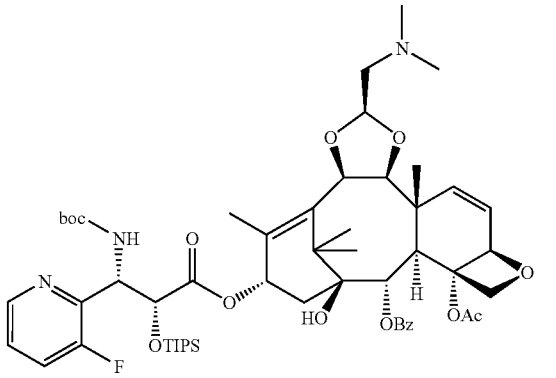

(in formula (9), boc, Ac, Bz and TIPS have the same meanings as above), and then reacting the compound of formula (9) with a palladium-carbon catalyst in the presence of hydrogen gas to thereby reduce it into a compound of the following general formula (10):

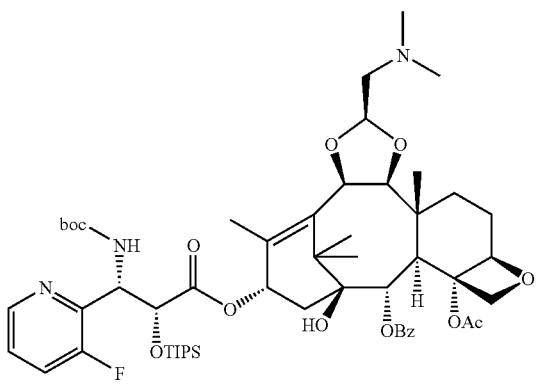

(10)

(in formula (12), boc, Ac, Bz and TIPS have the same meanings as above), and thereafter reacting it with a fluoroammonium salt to produce a compound of the following general formula (11) or its salt, or their hydrate or solvate:

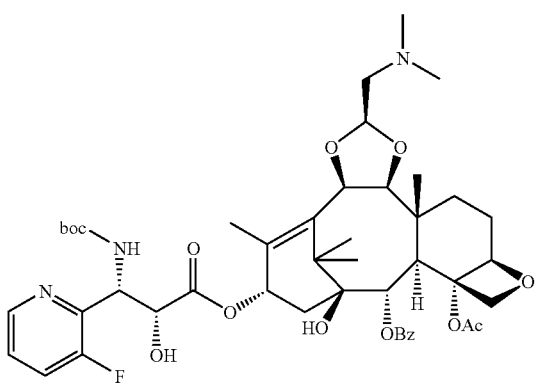

(11)

(in formula (11), boc, Ac and Bz have the same meanings as above).

Further, the invention relates to a novel intermediate (a compound of formula (12)) for obtaining a compound of the following general formula (16), and to a method of producing the compound of formula (16) that comprises using the intermediate. Specifically, the invention relates to a novel compound of the following general formula (12) or its salt, or their hydrate or solvate:

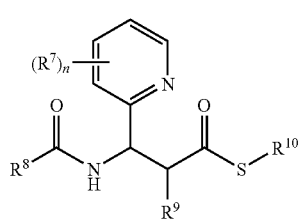

(12)

(in formula (12), $R^7$ means a halogen atom or an alkoxy group; n indicates an integer of from 0 to 4; when n is 2 or more, then two or more $R^7$'s may be the same or different; $R^8$ means an alkyl group, an aryl group or an alkoxy group, and the alkyl group, the aryl group or the alkoxy group may have one or more substituents selected from a group consisting of a halogen atom, a hydroxyl group, a carboxyl group, an alkyl group, an alkoxy group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group; $R^9$ means a hydroxyl group optionally having a protective group; $R^{10}$ means an alkyl group, an alkenyl group, an alkynyl group, a cycloalkyl group, an aryl group or a heterocyclic group, and the alkyl group, the alkenyl group, the alkynyl group, the cycloalkyl group, the aryl group or the heterocyclic group may have one or more substituents selected from a group consisting of a halogen atom, a hydroxyl group, a carboxyl group, an alkyl group, an alkoxy group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group). Further, the invention relates to a method for producing a compound of the following formula (16) or its salt, or their hydrate or solvate, which comprises reacting the compound of formula (12) with a compound of the following formula (15):

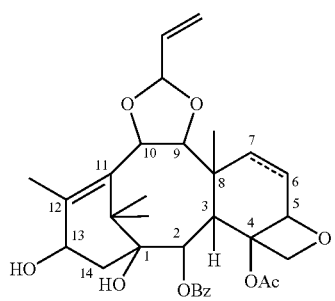

(15)

(in formula (15), the dot line part between the 6-position and the 7-position of the partial structure of the following formula (15-a):

(15-a)

means that the bond of this part may be a double bond; Ac means an acetyl group; Bz means a benzoyl group), to produce a compound of the following formula (16) or its salt, or their hydrate or solvate:

(16)

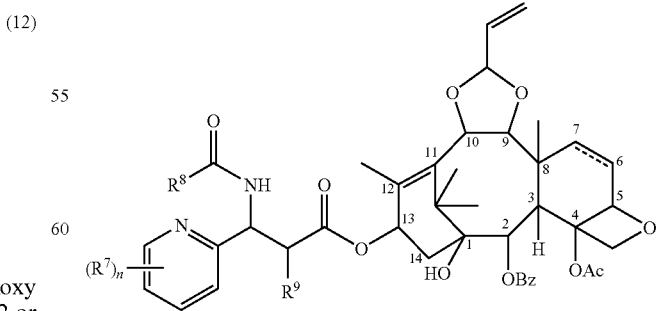

(in formula (16), $R^7$, $R^8$, $R^9$, n, Ac and Bz have the same meanings as above).

The novel compound of formula (12) is preferably a compound of the following general formula (13) or its salt, or their hydrate or solvate:

(13)

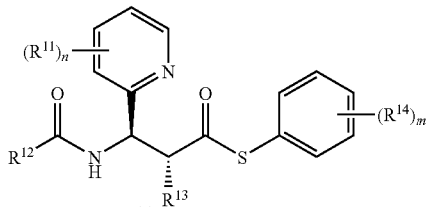

(in formula (13), $R^{11}$ means a halogen atom or an alkoxy group; n indicates an integer of from 0 to 4; when n is 2 or more, then two or more $R^{11}$'s may be the same or different; $R^{12}$ means an alkyl group, an aryl group or an alkoxy group, and the alkyl group, the aryl group or the alkoxy group may have one or more substituents selected from a group consisting of a halogen atom, a hydroxyl group, a carboxyl group, an alkyl group, an alkoxy group, a phenyl group, an amino group, an alkylamino group, an amino alkyl group, an alkylaminoalkyl group, an alkoxycarbonyl group, an aryloxycarbonyl group, an acyl group, an acylamino group and an acyloxy group; $R^{13}$ means a hydroxyl group optionally having a protective group; $R^{14}$ means a halogen atom, a pyrimidinyl group, a nitrile group, an acyl group or a methoxy group; m indicates an integer of from 0 to 5; when m is 2 or more, then two or more $R^{14}$'s may be the same or different). More preferably, the novel compound of formula (12) is a compound of the following general formula (14) or its salt, or their hydrate or solvate:

(14)

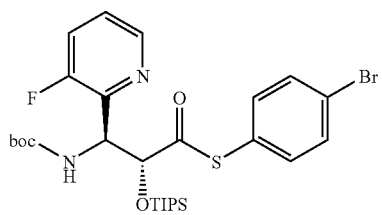

(in formula (14), boc means a tert-butoxycarbonyl group; TIPS means a triisopropylsilyl group).

Accordingly, the invention relates to a method for producing a compound of the following formula (18) or its salt, or their hydrate or solvate, which comprises reacting the compound of formula (13) with a compound of the following formula (17):

(17)

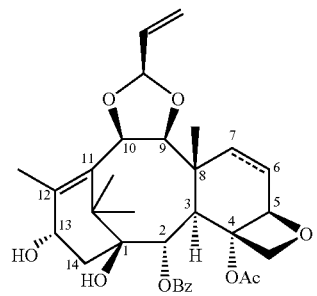

(in formula (17), the dot line part between the 6-position and the 7-position of the partial structure of the following formula (17-a):

(17-a)

means that the bond of this part may be a double bond; Ac means an acetyl group; Bz means a benzoyl group), to produce a compound of the following formula (18) or its salt, or their hydrate or solvate:

(18)

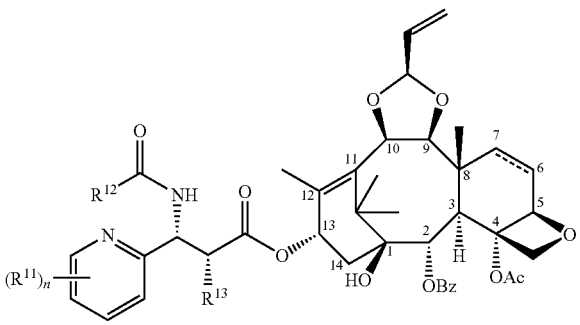

(in formula (18), $R^{11}$, $R^{12}$, $R^{13}$, n, Ac and Bz have the same meanings as above). More preferably, the invention relates to a method for producing a compound of the following general formula (7) or its salt, or their hydrate or solvate, which comprises reacting the compound of formula (14) with a compound of the following formula (19):

(19)

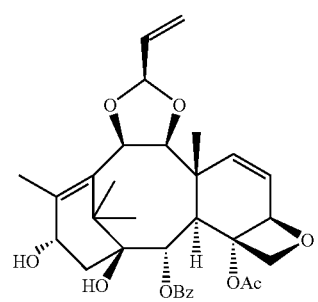

(in formula (19), Ac means an acetyl group; and Bz means a benzoyl group) to produce a compound of the following general formula (7) or its salt, or their hydrate or solvate:

(7)

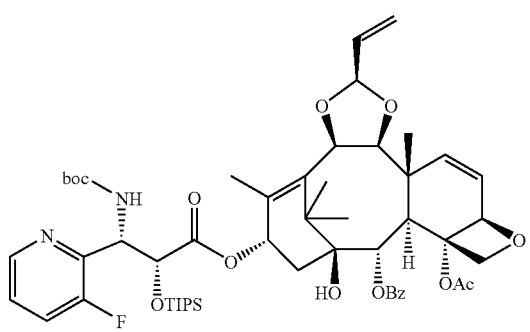

(in formula (7), boc, Ac, Bz and TIPS have the same meanings as above).

The compound of formula (7) obtained from the novel compound of formula (14) can be used for producing the compound of formula (11), which is a preferred embodiment of the intended taxan derivative of the invention, as so mentioned hereinabove. Accordingly, the invention further relates to a method for producing the compound of formula (13), using the novel compound of formula (14).

Specifically, the invention further relates to a method for producing the compound of formula (11) or its salt, or their hydrate or solvate, which comprises reacting the compound of formula (14) with the compound of formula (19) to produce the compound of formula (7), then reacting the compound of formula (7) with potassium permanganate in aqueous pyridin or in the presence of lithium hydroxide in aqueous pyridin to obtain the compound of formula (8), then reacting the compound of formula (8) with an alkali metal periodate and then with sodium acetoxyborohydride in the presence of acetic acid and dimethylamine to obtain the compound of formula (9), then reacting the compound of formula (9) with a palladium-carbon catalyst in the presence of hydrogen gas to reduce it into the compound of formula (10), and thereafter reacting it with a fluoroammonium salt to obtain the compound of formula (11) or its salt, or their hydrate or solvate.

EFFECT OF THE INVENTION

According to the invention, taxan derivatives having an antitumor effect can be produced, using low toxic and inexpensive materials. The method is efficient and inexpensive, and the product produced therein is readily purified. The invention is therefore suitable for industrial production of taxan derivatives.

BEST MODE FOR CARRYING OUT THE INVENTION

The compounds of the starting materials and the products in the invention are described.

"Alkyl group", "alkenyl group" and "alkynyl group" as referred to in this description may be linear or branched, and preferably have from 1 (2 for the alkenyl group and the alkynyl group) to 6 carbon atoms.

"Alkoxy group" means an alkyl group bonding to —O—, in which the alkyl group may be substituted with a phenyl group (optionally having a substituent). Its examples include a benzyloxy group, a phenethyloxy group, a p-methoxybenzyloxy group. Preferably, the alkyl moiety has from 1 to 6 carbon atoms.

"Alkoxycarbonyl group" means an alkyl group bonding to the oxygen atom of a group —COO—, in which the alkyl group may be substituted with a phenyl group (optionally having a substituent). Its examples include a benzyloxycarbonyl group, a phenethyloxycarbonyl group, a p-methoxybenzyloxycarbonyl group. Preferably, the alkyl moiety has from 1 to 6 carbon atoms.

"Aryl group" means a monovalent group derived from an aromatic hydrocarbon nucleus by removing one hydrogen atom from it, including, for example, a phenyl group, a tolyl group, a biphenylyl group, a naphthyl group.

In "aminoalkyl group", the amino group may bond to the alkyl group at any position thereof, and the alkyl group preferably has from 1 to 6 carbon atoms.

"Alkylamino group" means an amino group substituted with one alkyl group, or an amino group substituted with two alkyl groups (in which the two alkyl groups may be the same or different). Preferably, the alkyl group has from 1 to 6 carbon atoms.

"Acyl group" means a carbonyl group (—CO—) with a hydrogen atom, an alkyl group or an aryl group bonding thereto, and includes, for example, a formyl group, an acetyl group, a propanoyl group, a benzoyl group. The alkyl group bonding thereto preferably has from 1 to 6 carbon atoms; and the aryl group bonding thereto is preferably a phenyl group.

"Heterocyclic group" means a substituent derived from a monocyclic or bicyclic, saturated or unsaturated heterocyclic compound that contains one or more ring-constituting atoms selected from one or more types of atoms selected from a group consisting of an oxygen atom, a nitrogen atom and a sulfur atom, and the heterocyclic group may bond to the compound at any position thereof. The monocyclic heterocyclic group includes, for example, substituents derived from monocyclic heterocyclic compounds such as pyrrole, furan, thiophene, pyrrolidine, tetrahydrofuran, tetrahydrothiophene, imidazole, pyrazole, imidazolidine, pyrazolidine, oxazole, thiazole, oxadiazole, thiadiazole, pyridine, dihydropyridine, tetrahydropyridine, piperidine, pyridazine, pyrimidine, pyrazine, piperazine, dioxane, pyran, morpholine. The bicyclic heterocyclic group includes, for example, substituents derived from bicyclic heterocyclic compounds such as benzofuran, indolidine, benzothiophene, indole, naphthyridine, quinoxaline, quinazoline, chroman.

"Nitrogen-containing 5-membered or 6-membered saturated heterocyclic group of the formula (3-a) (in which X means an oxygen atom, a sulfur atom, $CH_2$, CH—Y, NH or N—Y; and Y means an alkyl group) (the heterocyclic group may have one or more alkyl groups on the carbon atom that constitutes the ring)" means a substituent derived from a 5-membered or 6-membered, saturated heterocyclic compound that inevitably contains one nitrogen atom as the constitutive atom of the heterocyclic group, and this includes, for example, substituents derived from pyrrolidine, imidazolidine, pyrazolidine, oxazolidine, thiazolidine, isoxazolidine, isothiazolidine, piperidine, piperazine, morpholine, thiomorpholine.

$R^1$ in formula (1) is preferably an aryl group, a heterocyclic group, an alkenyl group.

"Aryl group" for $R^1$ is preferably a phenyl group; "alkenyl group" for $R^1$ is preferably a 2-methyl-1-propenyl group. The heterocyclic group for $R^1$ is preferably a monocyclic heterocyclic group, more preferably a monocyclic, 5-membered or 6-membered heterocyclic group, and includes, for example, substituents derived from pyrrole, furan, thiophene, pyrrolidine, tetrahydrofuran, tetrahydrothiophene, imidazole, pyrazole, imidazolidine, pyrazolidine, oxazole, thiazole, oxadiazole, thiadiazole, pyridine, dihydropyridine, tetrahydropyran, piperidine, pyridazine, pyrimidine, pyrazine, piperazine, dioxane, pyran, morpholine. The heterocyclic group for $R^1$ is preferably a monocyclic, 5-membered or 6-membered heterocyclic group that contains one oxygen, nitrogen or sulfur atom as the constitutive atom of the ring structure thereof, including, for example, groups derived from pyrrole, furan, thiophene, pyrrolidine, tetrahydrofuran, tetrahydrothiophene, pyridine, dihydropyridine, tetrahydropyran, piperidine, pyran. More preferably, it is a monocyclic, 5-membered or 6-membered, unsaturated heterocyclic group that contains one oxygen, nitrogen or sulfur atom as the constitutive atom of the ring structure thereof, concretely including groups derived from furan, pyridine, pyrrole.

$R^1$ is especially preferably a 2-methyl-1-propenyl group, a phenyl group, a furyl group, a pyridyl group, a pyrrolyl group, even more preferably a pyridyl group optionally substituted with a halogen atom (preferably a fluorine atom) or an alkoxy group.

In formula (1), $R^2$ is a hydroxyl group optionally having a protective group. The protective group in $R^2$ includes a substituted silyl group, a benzyl group, a substituted benzyl group, a 1-ethoxyethyl group, a benzyloxycarbonyl group, a 2,2,2-trichloroethoxycarbonyl group. The substituent of the substituted silyl group includes an alkyl group, an aryl group and an aralkyl group; and the substituted silyl group includes a trimethylsilyl group, an isopropyldimethylsilyl group, a tert-butyldimethylsilyl group, a tribenzylsilyl group, a t-butyldiphenylsilyl group. The substituent of the substituted benzyl group includes a halogen atom, an alkyl group, an alkoxy group, a nitro group; and the substituted benzyl group includes a paranitrobenzyl group, a paramethoxybenzyl group. The protective group in $R^3$ is preferably a trialkylsilyl group such as triisopropylsilyl group, a tert-butyldimethylsilyl group, a triethylsilyl group, or a benzyl group, more preferably a triisopropylsilyl group or a benzyl group.

The compound of formula (1) is more preferably the compound of formula (4), even more preferably the compound of formula (7).

The alkyl group for $R^3$ in formula (3) preferably has from 1 to 6 carbon atoms, and is more preferably a methyl group, an ethyl group, a propyl group; the alkenyl group preferably has from 2 to 6 carbon atoms, and is more preferably an allyl group.

The substituent for the alkyl group, the alkenyl group or the phenyl group for $R^3$ is preferably an amino group, an alkylamino group, or a nitrogen-containing 5-membered or 6-membered saturated heterocyclic group of formula (3-a) (in which X means an oxygen atom, a sulfur atom, $CH_2$, CH—Y, NH or N—Y; and Y means a $C_1$-$C_3$ alkyl group) (the heterocyclic group may have an alkyl group on the carbon atom that constitutes the ring).

The alkyl moiety of the alkylamino group is preferably a $C_1$-$C_3$ alkyl group; and the alkylamino group may be dialkyl-substituted (in the dialkyl-substituted group, the two alkyl groups may be the same or different).

The nitrogen-containing 5-membered or 6-membered saturated heterocyclic group of formula (3-a) (the heterocyclic group may have one or more alkyl groups on the carbon atom that constitutes the ring) is more preferably a group derived from piperazine, morpholine, thiomorpholine or 4-$C_1$-$C_3$ alkylpiperazine. The alkyl group that may be a substituent on the ring-constituting carbon atom of the heterocyclic group is preferably a methyl group.

$R^3$ is more preferably a dimethylaminomethyl group or a morpholinomethyl group, even more preferably a dimethylaminomethyl group.

The compound of formula (3) is more preferably the compound of formula (6), even more preferably the compound of formula (11).

As so mentioned hereinabove, the invention is characterized in that the compound of formula (1) is processed with an alkali metal permanganese to produce the compound of formula (2) or its salt, or their hydrate or solvate (this may be hereinafter referred to as a step (b)).

"Alkali metal permanganate" for use in the invention includes sodium permanganate, potassium permanganate, cesium permanganate. Preferred is potassium permanganate. The molar ratio of "compound of formula (1)" to "alkali metal permanganate" is typically from 1/0.5 to 1/2, preferably from 1/1 to 1/1.5.

Although the base for use herein is not specifically limited, the base includes pyridine, potassium carbonate, triethylamine, sodium hydroxide, lithium hydroxide, aqueous ammonia, etc. Preferred are pyridine, lithium hydroxide, sodium hydroxide, aqueous ammonia; and more preferred are pyridine, lithium hydroxide. The molar ratio of "compound of formula (1)" to "base" is typically from 1/0.1 to 1/1, preferably from 1/0.2 to 1/0.8.

Although the solvent for use herein is not specifically limited as long as the solvent may be any one inert to the reaction. The solvent includes ether solvents such as aqueous tetrahydrofuran, aqueous 1,4-dioxane, aqueous dimethoxyethane; and other aqueous acetone, aqueous pyridine, aqueous acetone. Of those solvents, preferred are aqueous tetrahydrofuran, aqueous acetone and aqueous pyridine. More preferred is aqueous pyridine. The water content is typically from 10 to 40%, preferably from 20 to 40%, more preferably from 20 to 35%. "Aqueous" as referred to in this description for aqueous pyridine, aqueous tetrahydrofuran, aqueous acetone and other aqueous solvents means that the reaction system contains any of pyridine, tetrahydrofuran, acetone or other solvents, and water. Mixing pyridine, tetrahydrofuran, acetone or other solvents, with water may be attained before the reaction with other compound, or simultaneously with the reaction with other compound, or during the reaction.

The solvent may be the same as or different from the type of the above-mentioned base; and when the solvent and the base are the same, then they are preferably pyridine, more preferably aqueous pyridine.

The reaction temperature may fall generally within a range of from 0° C. to the boiling point of the solvent, preferably from 20° C. to the boiling point of the solvent, more preferably from 30° C. to 50° C. The reaction time may be generally from 5 minutes to 2 hours, preferably from 15 minutes to 1 hour.

In industrial-scale production of compounds, the amount of the solvent to the reaction substrate is a matter of importance to be investigated. When the amount of the solvent to the reaction substrate is smaller, then the production efficiency is higher. Preferably, the amount of the solvent to the reaction substrate in the step (b) is from about 10 to about 50 times, more preferably from 15 to 40 times, even more preferably from 15 to 30 times.

The compound of formula (1) in the invention can be produced, for example, according to the method described in JP-A-9-12578.

In the compound of formula (2) obtained in the invention, the group of —CH(OH)CH$_2$OH may be converted into the above-mentioned group —$R^3$ according to an ordinary known method (this may be hereinafter referred to as a step (c)); and optionally, when the bond between the 6-positioned carbon and the 7-positioned carbon in the compound is a double bond, then the compound may be processed for converting the double bond into a single bond (hereinafter this may be referred to as a step (d)), and/or when $R^2$ is a hydroxyl group having a protective group, then the compound may be processed for removing the protective group (hereinafter this may be referred to as a step (e)), thereby obtaining the compound of formula (3).

For converting the 1,2-diol group into the group $R^3$ (step (c)), the diol may be cleaved with an oxidizing agent such as an alkali metal periodate capable of oxidatively cleaving the 1,2-diol group, and then this may be reductively reacted with a corresponding compound ($R^3H$). For the reductive reaction, preferably used are an acid such as acetic acid and a reducing agent such as sodium acetoxyborohydride. When the group $R^3$ is a dimethylaminomethyl group, then the source of the dimethylamino group is preferably dimethylamine/methanol solution or dimethylamine hydrochloride, more preferably dimethylamine hydrochloride.

The alkali metal periodate for use in the step (c) includes lithium periodate, sodium periodate, potassium periodate, etc. Preferred is sodium periodate. The amount of the alkali metal periodate to be used may be calculated from the molar number of the compound of formula (1) used in the step (b), and the molar ratio of "compound of formula (1)" to "alkali metal periodate" may be typically from 1/1 to 1/4, preferably from 1/1 to 1/3, more preferably 1/2.

The solvent to be used in reacting the compound of formula (2) with an alkali metal periodate is not specifically defined, and may be anyone inert to the reaction. It includes ether solvents such as aqueous tetrahydrofuran, aqueous 1,4-dioxane, aqueous dimethoxyethane; alcohol solvents such as aqueous methanol, aqueous ethanol, aqueous 2-propanol; and other aqueous acetonitrile, aqueous pyridine, aqueous acetone, aqueous dimethylformamide. Of those solvents, preferred is aqueous acetonitrile. The water content is typically from 10 to 90%, preferably from 10 to 50%, more preferably from 15 to 30%.

When the compound of formula (2) is processed with an alkali metal periodate, a base may be or may not be added to it, but is preferably added thereto. Although the base to be added is not specifically limited, the base includes pyridine, potassium carbonate, sodium hydrogencarbonate, triethylamine, sodium hydroxide, lithium hydroxide, and is preferably pyridine.

The temperature at which the compound of formula (2) is processed with an alkali metal periodate may fall generally within a range of from 0° C. to the boiling point of the solvent, preferably from 20° C. to 50° C. The reaction time may be from about 30 minutes to 24 hours, typically from 2 hours to 18 hours.

The amount of the acid such as acetic acid to be used may be calculated from the molar number of the compound of formula (1) used in the step (b), and the molar ratio of "compound of formula (1)" to "acid" may be typically from 1/0.5 to 1/4, preferably from 1/1 to 1/2, more preferably 1/1.

The amount of $R^3H$ (e.g., dimethylamine) to be used may be calculated from the molar number of the compound of formula (1) used in the step (b), and the molar ratio of "compound of formula (1)" to "$R^3H$" may be typically from 1/0.5 to 1/4, preferably from 1/1 to 1/2, more preferably 1/1.5.

The amount of the reducing agent such as sodium acetoxyborohydride to be used may be calculated from the molar number of the compound of formula (1) used in the step (b), and the molar ratio of "compound of formula (1)" to "reducing agent (sodium acetoxyborohydride)" may be typically from 1/1 to 1/6, preferably from 1/2 to 1/4, more preferably 1/3.

Although the solvent to be used in reacting the compound of formula (2) with a reducing agent is not specifically limited as long as the solvent may be any one inert to the reaction, the solvent includes ether solvents such as tetrahydrofuran, 1,4-dioxane, dimethoxyethane; acetate solvents such as methyl acetate, ethyl acetate; and other acetonitrile, pyridine, dimethylformamide. Of those solvents, preferred are tetrahydrofuran and ethyl acetate.

The reaction temperature at which the compound of formula (2) is processed with a reducing agent may be generally within a range of from −78° C. to the boiling point of the solvent, preferably from 0° C. to the boiling point of the solvent, more preferably from 0° C. to 30° C.

The reaction time for which the compound of formula (2) is processed with a reducing agent may be from about 30 minutes to 5 hours, typically from 1 hour to 3 hours.

When the bond between the 6-positioned carbon and the 7-positioned carbon is a double bond, the reaction of converting the double bond into a single bond (step (d)) may be attained concretely by reacting the compound obtained in the above step (c) with a reduction catalyst such as palladium-carbon, platinum-carbon or ruthenium-carbon in the presence of hydrogen gas.

The hydrogen source in the step (d) may be hydrogen gas, formic acid or ammonium formate, but is preferably ammonium formate. From the hydrogen source, hydrogen is kept supplied to the reaction system until the reaction is substantially finished.

The amount of the catalyst such as palladium-carbon to be used may be calculated from the weight of the compound of formula (1) used in the step (b), and the ratio by weight of "compound of formula (1)" to "catalyst such as palladium-carbon catalyst" may be typically from 1/0.05 to 1/1, preferably from 1/0.1 to 1/0.5, more advantageously 1/0.25.

Although the solvent to be used is not specifically limited, the solvent includes alcohol solvents such as methanol, ethanol, 2-propanol; ether solvents such as tetrahydrofuran, 1,4-dioxane, dimethoxyethane; acetate solvents such as methyl acetate, ethyl acetate; and other acetonitrile, pyridine, dimethylformamide. Of those solvents, preferred is ethanol.

Though depending on the type of the solvent used, it may be advantageous to add water to the solvent. Typically, the water content is from 0 to 50%, preferably from 0 to 25%.

The reaction temperature may vary depending on the solvent used, but may fall generally within a range of from 0° C. to the boiling point of the solvent, preferably from 20° C. to 60° C.

The reaction time may be from about 1 hour to 3 days, and the reaction shall continue until it is substantially finished.

When $R^2$ is a hydroxyl group having a protective group, then the reaction to remove the protective group (step (e)) may be attained typically by reacting the compound obtained in the above step (b) or (c) with a fluoroammonium salt to deprotect it, though the condition for the deprotection may vary depending on the type of the protective group.

Although the fluoroammonium salt to be used in the step (e) is not specifically limited, the fluoroammonium salt is preferably tetrabutylammonium fluoride. The amount of the fluoroammonium salt to be used may be calculated from the molar number of the compound of formula (1) used in the step (b), and the ratio of "compound of formula (1)" to "fluoroammonium salt" may be typically from 1/0.5 to 1/10, but not specifically defined, the salt shall be supplied to the system until the reaction is substantially finished.

Although the solvent is not specifically limited as long as the solvent may be any one inert to the reaction, the solvent includes ether solvents such as tetrahydrofuran, 1,4-dioxane, dimethoxyethane; acetate solvents such as methyl acetate, ethyl acetate; alcohol solvents such as methanol, ethanol, 2-propanol; and other acetonitrile, pyridine, dimethylformamide. Of those solvents, preferred is ethyl acetate.

The reaction temperature may vary depending on the solvent used, but may fall generally within a range of from 0° C. to the boiling point of the solvent, preferably from 20° C. to the boiling point of the solvent.

The taxan derivative of formula (3) obtained in the invention may be isolated through recrystallization, after the reaction liquid has been processed. Although the solvent to be used for it is not specifically limited, the solvent includes alcohol solvents such as aqueous methanol, aqueous ethanol, aqueous 2-propanol; ether solvents such as aqueous tetrahydrofuran, aqueous 1,4-dioxane, aqueous dimethoxyethane; and other aqueous acetone, aqueous acetonitrile, aqueous N,N-dimethylformamide. Of those solvents, preferred is aqueous acetone. The water content of the solvent may be from 10 to 90%, preferably from 20 to 60%, more preferably from 20 to 40%.

As mentioned hereinabove, the compound of formula (3) that is to be finally obtained in the invention is preferably the compound of formula (6), more preferably the compound of formula (11).

A method for producing the compound of formula (11) according to the invention is described concretely hereinunder.

Specifically, the more preferred embodiment of the invention comprises producing the compound of formula (8) by reacting the compound of formula (7) with an alkali metal permanganate in the presence of a base (step (b)).

Further, according to the invention, the compound (7) may be processed with potassium permanganate in aqueous pyridin, or in the presence of lithium hydroxide in aqueous pyridine to obtain the compound of formula (8) (step (b)); then the compound (8) is processed with an alkali metal periodate, and then processed with sodium acetoxyborohydride in the presence of acetic acid and dimethylamine to obtain the compound of formula (9) (step (c)); and optionally, the compound (9) is processed with a palladium-carbon catalyst in the presence of hydrogen gas to reduce it into the compound of formula (10); and thereafter optionally, this is processed with a fluoroammonium salt for deprotection (step (e)) to produce the compound of formula (11) or its salt, as in the process shown below.

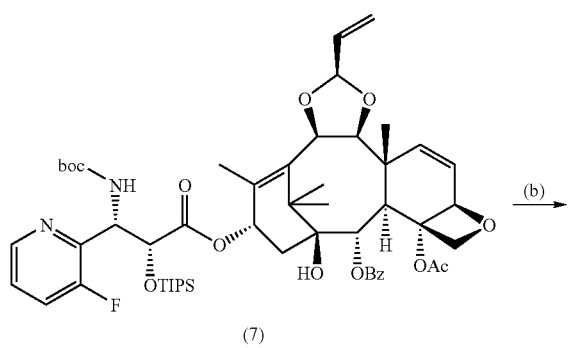

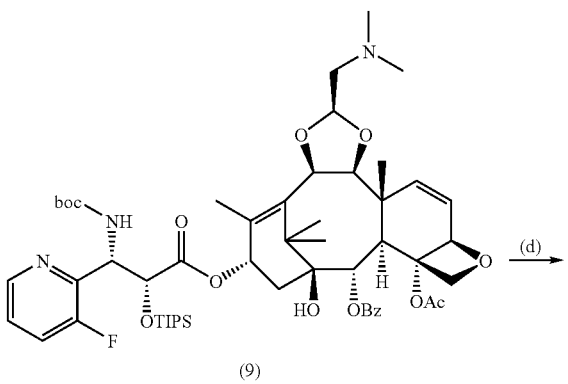

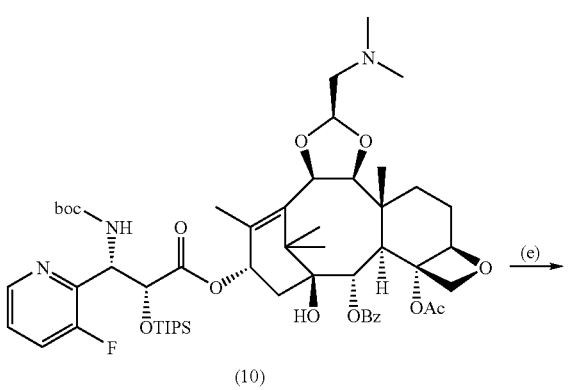

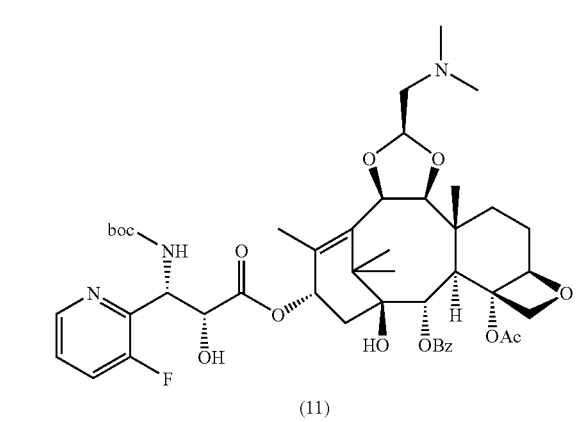

In the formulae, boc means a tert-butoxycarbonyl group; TIPS means a triisopropylsilyl group; Ac means an acetyl group; Bz means a benzoyl group.

The compound (7) may be obtained according to the method described in JP-A-2002-332287, but may be produced by reacting a novel compound of formula (14) with a compound of formula (19), as in the process (a) mentioned below. The novel compound (14) may be obtained through thiol-esterification (in this description, this may be referred to as thio-esterification) of {(3R,4S)-1-(tert-butoxycarbonyl)-4-(3-fluoro-2-pyridyl)-3-triisopropylsilyloxy-2-azetidinone} of formula (20) with 4-bromothiophenol, as in the process mentioned below. The compound (20) may be obtained according to the method described in JP-A-2002-332287.

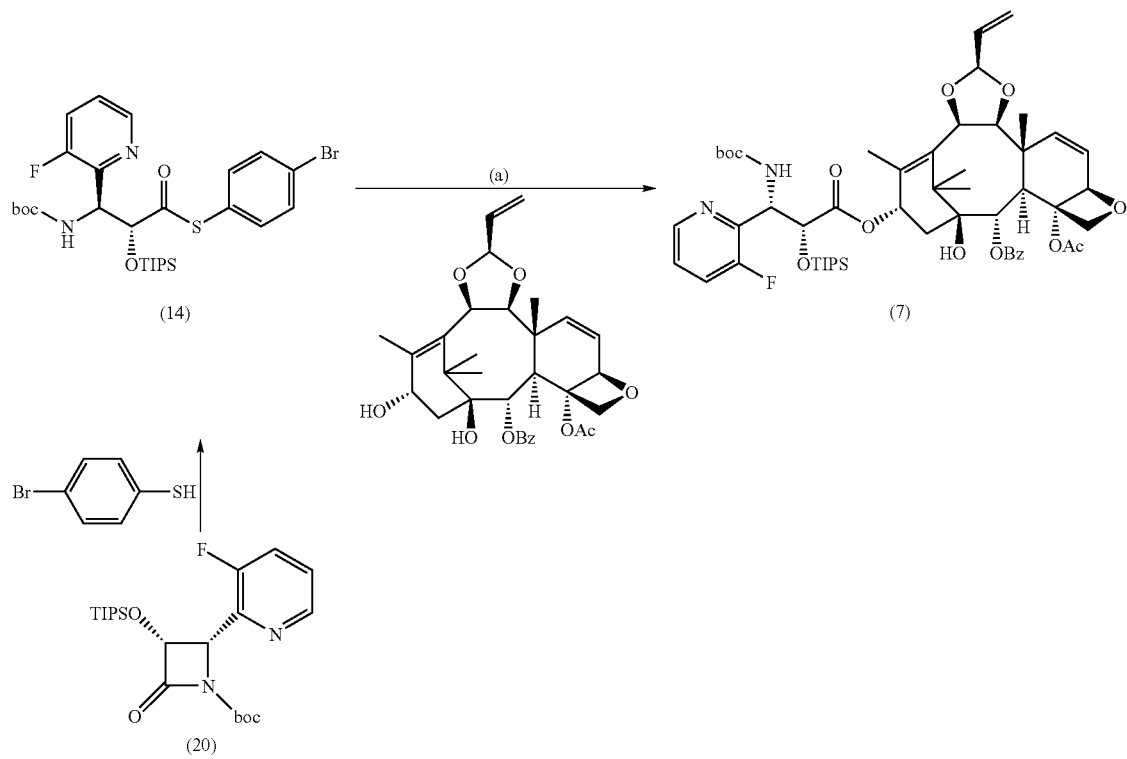

The compound (14) may be obtained through thio-esterification of the compound (20) with 4-bromothiophenol.

The compound (14) may be obtained by reacting the compound (20) with a thiol group-having compound in any ordinary manner. Concretely, for example, the compound (14) may be obtained by reacting the compound (20) with a thiol group-having compound in a suitable solvent optionally in the presence of a base. The thiol group-having compound includes 4-bromobenzenethiol, 4-chlorobenzenethiol, 2-mercaptoimidazole, etc, to which, however, the invention should not be limited. The thiol group-having compound is preferably 4-bromobenzenethiol and 4-chlorobenzenethiol, more preferably 4-bromobenzenethiol.

The thio-esterification is preferably effected in the presence of a base. Although the base is not specifically limited, the base includes amines such as 4-(dimethylamino)pyridine, triethylamine, N,N-pyridine; and alkali or alkaline earth metal salts such as potassium carbonate, sodium carbonate, cesium carbonate, calcium carbonate, but is preferably potassium carbonate. The amount of the base to be used may vary depending on the type of the base used. The ratio by weight of the compound (20) to the base is typically from 1/0.001 to 1/1, preferably from 1/0.1 to 1/0.3.

Although the solvent is not specifically limited as long as the solvent may be any one inert to the reaction, the solvent includes ether solvents such as diisopropyl ether, diethyl ether, tetrahydrofuran, 1,4-dioxane, dimethoxyethane; ester solvents such as ethyl acetate, methyl acetate; ketone solvents such as acetone, methyl isobutyl ketone; amide solvents such as N,N-dimethylformamide, 1,3-dimethylimidazolidinone; hydrocarbon solvents such as n-heptane, n-hexane, cyclohexane; and other acetonitrile, pyridine, toluene, etc. Of those solvents, preferred is diisopropyl ether.

The reaction temperature may fall generally within a range of from 0° C. to the boiling point of the solvent, preferably from 15° C. to the boiling point of the solvent. The reaction time may be from about 1 minute to 36 hours, typically from 5 minutes to 3 hours.

Another method for producing the compound (14) comprises protecting the side branch of a carboxylic acid-type taxan derivative with a suitable protective group and then thio-esterifying the derivative with 4-bromothiophenol. A method for producing the side branch of a carboxylic acid-type taxan derivative is disclosed, for example, in the following references: *J. Org. Chem.*, 1991, 56, 6939-6942; *J. Org. Chem.*, 1993, 58, 255-257; *J. Org. Chem.*, 1994, 59, 1238-1240; *Tetrahedron Asymmetry*, Vol. 7, No. 1, 243-262, 1996; *Tetrahedron Letters*, 44 (2003) 8685-8687.

For obtaining the compound (7) from the compound (14) (step (a)), the compound (14) may be reacted with a compound (19) in an inert solvent in the presence of a base to give the compound (7). The compound (19) may be obtained according to the method described in JP-A-2002-332287.

The molar ratio of the compound (19) to the compound (14) may be typically from 1/1 to 1/3, preferably 1/1.5.

The reaction is preferably effected in the presence of a base. Although the base is not specifically limited, the base includes alkali metal hydrides such as sodium hydride, lithium hydride, potassium hydride; alkali metal amides such as lithium diisopropylamide, but is preferably sodium hydride. The molar ratio of the compound (19) to the base may be typically from 1/1 to 1/6, preferably from 1/2 to 1/4.

Although the solvent is not specifically limited as long as the solvent may be any one inert to the reaction, the solvent includes ether solvents such as tetrahydrofuran, diethyl ether, 1,4-dioxane, dimethoxyethane; and other acetonitrile, ethyl acetate, dimethylformamide, toluene, etc. Of those solvents, preferred are ether solvents, and more preferred is dimethoxyethane.

The reaction temperature may vary depending on the solvent used, but may be generally within a range of from −78° C. to the boiling point of the solvent, preferably from 0° C. to 30° C. The reaction shall continue generally for about 10 minutes to 10 hours, typically for 1 hour to 5 hours until it is substantially finished.

This step is preferably effected in an inert gas atmosphere such as nitrogen or argon.

The compound (7) may be isolated through recrystallization after the reaction liquid has been processed. Although the solvent for it is not specifically limited, the solvent includes alcohol solvents such as methanol, ethanol, 2-propanol; ether solvents such as diisopropyl ether; and other acetonitrile, ethyl acetate, toluene, etc. Of those solvents, preferred is ethanol.

The purity of the recrystallized compound (7) may be further increased through slurry purification thereof. The solvent to be used for it includes hydrocarbon solvents such as hexane, heptane, cyclohexane and their mixtures; alcohol solvents such as methanol, ethanol, isopropanol; and other diisopropyl ether, acetonitrile, etc. Of those solvents, preferred is a hexane/cyclohexane mixture.

The compound (7) obtained in the above step (a) may be further processed in the step (b) to the step (e) to obtain the compound (11). The step (b) to the step (e) and the method for purifying the compound of formula (11) obtained after the steps are as described hereinabove.

Further according to the invention, the process of the step (a) to the step (e) may be carried out on an industrial scale, and the intended taxan derivative of formula (3) can be obtained efficiently.

The compound obtained in the invention may be a free form, but may also be an acid-addition salt. The acid-addition salt includes inorganic acid salts such as hydrochlorides, sulfates, nitrates, hydrobromides, hydroiodides, phosphates; and organic salts such as acetates, methanesulfonates, benzenesulfonates, toluenesulfonates, citrates, maleates, fumarates, lactates. In addition, the compound may also be a hydrate or a solvate, for which the solvent includes methanol, ethanol, propanol, butanol, acetone, acetonitrile, benzene, toluene, tetrahydrofuran, N,N-dimethylformamide, etc.

The compound obtained in the invention may be used as medicines and may treat cancers on the basis of its antitumor effect. The subject for the treatment includes various cancers such as lung cancer, digestive organ cancer, ovarian cancer, uterine cancer, breast cancer, liver cancer, cervicocerebral cancer, blood cancer, renal cancer, testicles tumor, etc.

The compound obtained in the invention can be administered as various injections for intravenous injection, intramuscular injection or subcutaneous, or in other various routes such as oral administration or percutaneous administration. Of such administration routes, preferred is oral administration from the viewpoint of attaining the effects mentioned hereinunder. For oral administration, the compound may be either a free form or a salt thereof.

For preparing medicines and antitumor agents, suitable preparations may be selected depending on their administration routes, and they may be prepared in various formulation methods generally employed for preparing various preparations. The preparation form of the antitumor agent of the invention for oral administration includes, for example, tablets, powders, granules, capsules. The other preparation forms are solutions, syrups, elixirs, oily or aqueous suspensions. Of those, preferred are capsules, tablets and solutions. The injections may contain a stabilizer, a preservative or a dissolution promoter, etc. A solution which may contain these auxiliary additives may be lyophilized into a solid preparation, which may be formed into a liquid injection before use.

The liquid preparations include solutions, suspensions and emulsions. In preparing these preparations, a suspending agent and an emulsifier may be added thereto as additives.

The compound of the invention may be used for treatment of cancer of mammals, especially humans. In case where the compound is administered to a human, then it is desirable that the compound is administered once a day and repeatedly at suitable intervals.

The dose of the compound is preferably from about 0.5 mg to 50 mg, more preferably from about 1 mg to 20 mg per m$^2$ of the body surface of a case to which the compound is to be administered.

EXAMPLE

The invention is described in detail with reference to the following Examples, to which, however, the invention should not be limited.

In this description, the following abbreviations may be used for simplification.

Boc: tert-butoxycarbonyl group.

Ac: acetyl group.

Bz: benzoyl group.

TIPS: triisopropylsilyl group.

Compound 19: (1S,2S,3R,4S,5R,8R,9S,10R,13S)-4-Acetoxy-2-benzoyloxy-5,20-epoxy-1,13-dihydroxy-9,10-[(1S)-2-propenylidenedioxy]tax-6,11-diene.

Compound 14: S-(4-Bromophenyl)(2R,3S)-3-[(tert-butoxycarbonyl)amino]-3-(3-fluoro-2-pyridinyl)-2-[(triisopropylsilyl)oxy]propanethioate.

Compound 7: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-6,1,1-dien-13-yl(2R,3S)-3-(tert-butoxycarbonylamino)-3-(3-fluoro-2-pyridyl)-2-triisopropylsilyloxypropionate.

Compound 8: (1S,2S,3R,4S,5R,8R,9S,10R,13S)-4-Acetoxy-2-benzoyloxy-5,20-epoxy-1-hydroxy-9,10-[(1S)-2,3-dihydroxypropylidenedioxy]tax-6,11-dien-13-yl(2R,3S)-3-(tert-butoxycarbonylamino)-3-(3-fluoro-2-pyridyl)-2-triisopropylsilyloxypropionate.

Compound 9: (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-6,11-dien-13-yl(2R,3S)-3-(tert-butoxycarbonylamino)-3-(3-fluoro-2-pyridyl)-2-triisopropylsilyloxypropionate.

Compound 10: (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl(2R,3S)-3-(tert-butoxycarbonylamino)-3-(3-fluoro-2-pyridyl)-2-triisopropylsilyloxypropionate.

Compound 11: (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl(2R,3S)-3-(tert-butoxycarbonylamino)-3-(3-fluoro-2-pyridyl)-2-hydroxypropionate.

Example 1

Confirmation of Dihydroxylation of Compound 7 with Potassium Permanganate ($KMnO_4$)

Herein confirmed was whether or not the compound 7 could be dihydroxylated with $KMnO_4$. 100 mg (0.0995 mmol) of the compound 7 was dissolved in 2 mL of a solvent and water ($H_2O$), and at room temperature, 0.0995 mmol of $KMnO_4$ was added thereto. The progress of the reaction was investigated through HPLC. The result is shown in Table 1.

content of the solvent was increased, then the reaction went on in acetone or THF. The compound 7 was insoluble in acetonitrile.

Example 2

Influence of Solvent on Dihydroxylation of Compound 7 with $KMnO_4$

Other reaction solvents other than THF and acetone used in Example 1 were tested. Solvents capable of dissolving the compound 7 and capable of accepting the reaction as a mixed solvent thereof with water were investigated. As a result, it was found that, of 11 types of solvents (pyridine, acetylacetone, dimethoxyacetone, ether, piperidine, triethylamine, dimethylformamide, dimethylsulfoxide, acetic acid, acetic anhydride), pyridine is good for the reaction. 100 mg (0.0995 mmol) of the compound 7 was dissolved in pyridine, $H_2O$ was added, and $KMnO_4$ was added thereto. After 15 minutes, the progress of the reaction was analyzed through HPLC. The result is shown in Table 2. In Table 2, "area %" means the ratio of each peak area to the total sum of all the peak areas, as calculated on the basis of each peak area obtained in HPLC.

TABLE 2

| | Solvent | | | | | | | Product (area %) | | |
|---|---|---|---|---|---|---|---|---|---|---|
| | Pyridine (mL) | Ratio of pyridine (volume) to compound 7 (mass) | Acetone (mL) | Ratio of acetone (volume) to compound 7 (weight) | $H_2O$ (mL) | Ratio of water (volume) to compound 7 (weight) | Oxidizing Agent $KMnO_4$ (mmol) | Compound 8 | Compound 7 | Others |
| 1 | 1 | 10 | 1 | 10 | 0.7 | 7 | 0.209 | 69.5 | n.d.[a] | 6.8 |
| 2 | 2 | 20 | 0 | 0 | 1 | 10 | 0.209 | 75.9 | n.d. | 4.9 |
| 3 | 2 | 20 | 0 | 0 | 1 | 10 | 0.149 | 85.5 | n.d. | 4.5 |
| 5 | 2 | 20 | 0 | 0 | 0.5 | 5 | 0.119 | 65.3 | 14.0 | 6.1 |
| 6 | 3 | 30 | 0 | 0 | 0 | 0 | 0.209 | trace | — | — |
| 7 | 1.5 | 15 | 0 | 0 | 0.75 | 7.5 | 0.119 | 82.4 | 2.0 | 3.4 |
| 8 | 1 | 10 | 0 | 0 | 0.5 | 5 | 0.119 | 82.5 | 0.6 | 4.7 |

[a] n.d. means "not detected".

TABLE 1

| | Solvent | Water (μL) | Time (hrs) | Proportion of Compound 8 in Product (%) |
|---|---|---|---|---|
| 1 | acetone | 20 | 2 | 8.8 |
| 2 | acetone | 200 | 2 | 43.0 |
| 3 | acetone | 200 | 4 | 43.2 |
| 4 | tetrahydrofuran | 20 | 2 | 3.2 |
| 5 | tetrahydrofuran | 200 | 2 | 37.5 |
| 6 | tetrahydrofuran | 200 | 4 | 38.0 |
| 7 | acetonitrile | 20 | 2 | 4.5 |
| 8 | acetonitrile | 200 | 2 | 11.1 |

This experiment confirmed the dihydroxylation of the compound 7 with $KMnO_4$. The reaction went on in a solvent of acetone or tetrahydrofuran (THF), in which, however, a large amount of impurities were formed. When the water The above experiment confirmed the dihydroxylation of the compound 7 with $KMnO_4$ in the solvent pyridine. It shows that, when water is not added to the solvent pyridine, then the reaction does not go on (Case 6).

Example 3

Influence of Base on Dihydroxylation of Compound 7 with $KMnO_4$

The influence, if any, of a base on the dihydroxylation of the compound 7 with $KMnO_4$ was investigated. 50 mg of the compound 7 (0.0497 mmol) dissolved in a solvent was reacted with $KMnO_4$ at room temperature in the presence of various bases, and the progress of the reaction was investigated through HPLC. The result is shown in Table 3.

In Table 3, "area %" means the ratio of each peak area to the total sum of all the peak areas, as calculated on the basis of each peak area obtained in HPLC.

TABLE 3

| | | Solvent | | | | | | | Product (area %) | | |
|---|---|---|---|---|---|---|---|---|---|---|---|
| | | Ratio of pyridine | | Ratio of THF | | Ratio of water | | | Base | | |
| | Pyridine (mL) | (volume) to compound 7 (weight) | THF (mL) | (volume) to compound 7 (weight) | Water (mL) | (volume) to compound 7 (weight) | Oxidizing Agent $KMnO_4$ (mmol) | Type (concentration: mmol) | Compound 8 | Total of impurities | Residual starting materials |
| 1 | 1 | 20 | 0 | 0 | 0.675 | 13.5 | 0.0746 | no | 71 | 27 | 2.2 |
| 2 | 1 | 20 | 0 | 0 | 0.675 | 13.5 | 0.0746 | potassium carbonate (0.249) | 73 | 20 | 7.2 |
| 3 | 1 | 20 | 0 | 0 | 0.675 | 13.5 | 0.0746 | TEA (0.149) | 58 | 15 | 27 |
| 4 | 1 | 20 | 0 | 0 | 0.675 | 13.5 | 0.0746 | LiOH (0.0497) | 88 | 9.5 | 2.4 |
| 5 | 1 | 20 | 0 | 0 | 0.675 | 13.5 | 0.0746 | NaOH (0.0497) | 84 | 14 | 2.3 |
| 6 | 1.5 | 30 | 0 | 0 | 0.550 | 11 | 0.0647 | LiOH (0.0373) | 88 | 12 | 0.2 |
| 7 | 0 | 0 | 1.5 | 30 | 0.550 | 11 | 0.124 | LiOH (0.0373) | 90 | 9.3 | 0.7 |

Adding a base to the reaction system reduced the formation of impurities. This may be because the base added to the system would control the reactivity of $KMnO_4$ having a strong oxidizing potency to such that $KMnO_4$ could promote the oxidation not too much decomposing the starting substance.

Example 4

Influence of the Volume of Solvent on Dihydroxylation of Compound 7 with $KMnO_4$ In industrial scale production of compounds, the amount of the solvent to the reaction substrate is also a matter of importance to be investigated. When the amount of the solvent relative to the reaction substrate is smaller, then the production efficiency is higher. Accordingly, herein investigated was the influence of the amount of a solvent, aqueous pyridin on the dihydroxylation of the compound 7 with $KMnO_4$.

The amount of the compound 7 (50 mg, 0.0497 mmol), $KMnO_4$ (0.0647 mmol) and lithium hydroxide (0.00995 mmol) were kept constant, and the ratio of aqueous pyridine (volume) to the compound 7 (weight) was varied. The result is shown in Table 4. In Table 4, "area %" means the ratio of each peak area to the total sum of all the peak areas, as calculated on the basis of each peak area obtained in HPLC.

TABLE 4

| | | Solvent | | Product (area %) | |
|---|---|---|---|---|---|
| | aqueous pyridine (mL) | ratio of aqueous pyridine (volume) to compound 7 (weight) | water content (%) | compound 8 | compound 7 |
| 1 | 1.50 | 30 | 30 | 89.0 | 0.0 |
| 2 | 1.25 | 25 | 30 | 88.4 | 0.0 |
| 3 | 1.00 | 20 | 30 | 87.5 | 0.0 |
| 4 | 0.75 | 15 | 30 | 86.3 | 0.1 |
| 5 | 1.50 | 30 | 25 | 87.0 | 0.3 |
| 6 | 1.25 | 25 | 25 | 87.9 | 0.1 |
| 7 | 1.00 | 20 | 25 | 87.7 | 0.0 |
| 8 | 0.75 | 15 | 25 | 87.6 | 0.0 |

The above experiment shows that, when the ratio of aqueous pyridine (volume) to the compound 7 (weight) is 15 times or more, then the compound 8 is produced well (comparison between case 1 and case 4, or comparison between case 5 and case 8).

Example 5

Production of (1S,2S,3R,4S,5R,8R,9S,10R,13S)-4-acetoxy-2-benzoyloxy-5,20-epoxy-1-hydroxy-9,10-[(1S)-2-propenylidenedioxy]tax-6,11-dien-13-yl(2R,3S)-3-(tert-butoxycarbonylamino-3-(3-fluoro-2-pyridyl)-2-triisopropylsilyloxypropionate (compound 7)

Production of S-(4-bromophenyl)(2R,3S)-3-[(tert-butoxycarbonyl)amino]-3-(3-fluoro-2-pyridinyl)-2-[(triisopropylsilyl)oxy]propanethioate (compound 14)

A concentrated residue (70.9 mmol) of (3R,4S)-1-(tert-butoxycarbonyl)-4-(3-fluoro-2-pyridyl)-3-triisopropylsilyloxy-2-azetidinone (compound 20) was dissolved in diisopropyl ether (240 mL), and 4-bromothiophenol (15.5 g, 82.0 mmol) and potassium carbonate (3 g) were added thereto, and stirred at room temperature for 25 minutes. The disappearance of (3R,4S)-1-(tert-butoxycarbonyl)-4-(3-fluoro-2-pyridyl)-3-triisopropylsilyloxy-2-azetidinone was confirmed, and then water (200 mL) and diisopropyl ether (120 mL) were added thereto and subjected to liquid-liquid separation. The organic layer was separated, washed with water (150 mL) and then with saturated saline water (150 mL), dried over magnesium sulfate, and concentrated under reduced pressure to obtain a residue of S-(4-bromophenyl)(2R,3S)-3-[(tert-butoxycarbonyl)amino]-3-(3-fluoro-2-pyridinyl)-2-[(triisopropylsilyl)oxy]propanethioate (compound 14) (45.3 g).

Compound 14: S-(4-Bromophenyl)(2R,3S)-3-[(tert-butoxycarbonyl)amino]-3-(3-fluoro-2-pyridinyl)-2-[(triisopropylsilyl)oxy]propanethioate $^1$H-NMR (400 MHz, $CDCl_3$, TMS) δ: 1.07-1.10 (21H, m), 1.42 (9H, s), 4.82 (1H, d, J=4.2 Hz), 5.58 (1H, dd, J=9.5, 4.2

Hz), 6.10 (1H, d, J=9.5 Hz), 7.18 (2H, d, J=8.5 Hz), 7.25-7.30 (1H, m), 7.41 (1H, t, J=8.8 Hz) 7.52 (2H, dt, 8.5, 2.2 Hz) 8.39 (1H, d, J=4.6 Hz).

<Production of Compound 7>

Dimethoxyethane (179 mL) was added to sodium hydride (6.37 g, content 55%, 146 mmol), and the system was purged with nitrogen gas. With cooling with ice-cold water, (1S,2S,3R,4S,5R,8R,9S,10R,13S)-4-acetoxy-2-benzoyloxy-5,20-epoxy-1,13-dihydroxy-9,10-[(1S)-2-propenylidenedioxy]tax-6,11-diene (25.5 g, 44.9 mmol) dissolved in dimethoxyethane (204 mL) was dropwise added thereto. Next, the above reaction residue, S-(4-bromophenyl)(2R,3S)-3-[(tert-butoxycarbonyl)amino]-3-(3-fluoro-2-pyridinyl)-2-[(triisopropylsilyl)oxy]propanethioate (45.0 g, about 67.4 mmol) dissolved in dimethoxyethane (128 mL) was dropwise added thereto, taking 10 minutes. Then, cooling the system with ice-cold water was stopped, and this was stirred for about 1 hour. The termination of the reaction was confirmed, and then this was extracted with aqueous 4% sodium hydrogencarbonate solution (300 mL) and ethyl acetate (500 mL) added thereto, and subjected to liquid-liquid separation. The organic layer was taken out, washed with saturated saline water (300 mL), and then concentrated under reduced pressure. Ethanol (510 mL) was added to the concentrated residue, dissolved under heat at 50° C., and stirred overnight at room temperature. Next, this was further stirred for 4 hours with cooling with ice-cold water, and the precipitated crystal was taken out through filtration. The precipitate was formed into slurry with heptane (530 mL), filtered, and dried under reduced pressure at 50° C. to obtain the entitled compound (31.7 g, 31.5 mmol).

Compound 7: (1S,2S,3R,4S,5R,8R,9S,10R,13S)-4-Acetoxy-2-benzoyloxy-5,20-epoxy-1-hydroxy-9,10-[(1S)-2-propenylidenedioxy]tax-6,11-dien-13-yl(2R,3S)-3-(tert-butoxycarbonylamino-3-(3-fluoro-2-pyridyl)-2-triisopropylsilyloxypropionate

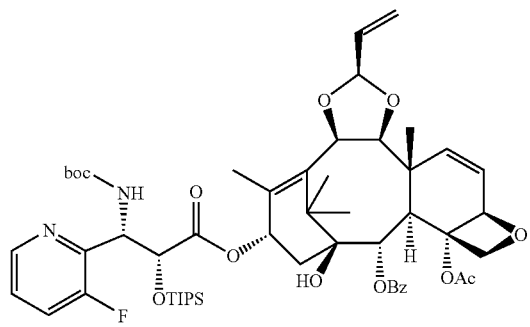

(7)

$^1$H-NMR (400 MHz, CDCl$_3$, TMS) δ: 0.88-0.92 (21H, m), 1.33 (3H, s), 1.38 (9H, s), 1.56 (3H, s), 1.60 (3H, s), 1.76 (3H, s), 2.41-2.45 (2H, m), 2.51 (3H, s), 3.14 (1H, d, J=5.8 Hz), 4.06 (1H, d, J=7.8 Hz), 4.33 (2H, s), 4.90 (1H, d, J=4.4 Hz), 4.94 (1H, d, J=2.4 Hz), 5.19-5.22 (2H, m), 5.48 (1H, d, J=10.3 Hz), 5.58-5.64 (2H, m), 5.70 (1H, dd, J=10.3, 4.4 Hz), 5.96-6.14 (5H, m), 7.26-7.30 (1H, m), 7.41 (1H, t, J=8.5 Hz), 7.49 (2H, t, J=7.5 Hz), 7.59 (1H, t, J=7.5 Hz), 8.17 (2H, d, J=7.5 Hz), 8.40 (1H, d, J=4.4 Hz).

Example 6

Production Method 1 for (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl(2R,3S)-3-(tert-butoxycarbonylamino-3-(3-fluoro-2-pyridyl)-2-hydroxypropionate (Compound 11)

Pyridine (39 L) and water (9.2 L) were added to (1S,2S,3R,4S,5R,8R,9S,10R,13S)-4-acetoxy-2-benzoyloxy-5,20-epoxy-1-hydroxy-9,10-[(1S)-2-propenylidenedioxy]tax-6,11-dien-13-yl(2R,3S)-3-(tert-butoxycarbonylamino)-3-(3-fluoro-2-pyridyl)-2-triisopropylsilyloxypropionate (compound 7) (1.31 kg, 1.30 mol), and stirred at room temperature, and aqueous 1 N sodium hydroxide solution (0.98 L, 0.98 mol) and aqueous 50 g/L potassium permanganate solution (5.35 L, 1.69 mol) were added thereto, and stirred for about 30 minutes. Ethyl acetate, aqueous 10% citric acid solution and saturated saline water were added to the reaction mixture, extracted and subjected to liquid-liquid separation. The organic layer was taken out, washed with a mixture of aqueous 10% citric acid solution and saturated saline water, and then with a mixture of aqueous 4% sodium hydrogencarbonate solution and saturated saline water, and concentrated under reduced pressure to obtain a residue of (1S,2S,3R,4S,5R,8R,9S,10R,13S)-4-acetoxy-2-benzoyloxy-5,20-epoxy-1-hydroxy-9,10-[(1S)-2,3-dihydroxypropylidenedioxy]tax-6,11-dien-13-yl(2R,3S)-3-(tert-butoxycarbonylamino)-3-(3-fluoro-2-pyridyl)-2-triisopropylsilyloxypropionate (compound 8).

The residue was dissolved in acetonitrile (26 L), and sodium periodate (0.557 kg, 2.61 mol) dissolved in pyridine (1.3 L) and water (5.2 L) was added thereto, and stirred at room temperature for about 5 hours. The termination of the reaction was confirmed, and aqueous 20% sodium thiosulfate solution was added thereto and stirred for a while. Then, this was filtered through Celite, and the filtrate was concentrated under reduced pressure. The concentrated liquid was extracted with ethyl acetate, the organic layer was taken out, washed twice with a mixture of 2 N hydrochloric acid and saturated saline water, and then once with a mixture of 4% sodium hydrogencarbonate and saturated saline water. The organic layer was dried over magnesium sulfate, then concentrated under reduced pressure, and tetrahydrofuran (13 L), acetic acid (74.5 mL, 1.30 mol), and 2 mol/L dimethylamine-methanol solution (0.98 L, 1.95 mol) were added thereto, and stirred with cooling with ice-cold water. Sodium acetoxyborohydride (552 g, 2.00 mol) was added to it, and stirred for about 2 hours. Then, the termination of the reaction was confirmed, and this was extracted with 4% sodium hydrogencarbonate and ethyl acetate added thereto, and subjected to liquid-liquid separation. The organic layer was washed with a mixture of water and saturated saline water, then dried over magnesium sulfate, and concentrated to dryness under reduced pressure to obtain a residue of (1S,2S,3R,4S,5R,8R,9S,10R,13S)-4-acetoxy-2-benzoyloxy-9,10[(1S)-2-(dimethylamino)ethylidenedioxy]-5,20-epoxy-1-hydroxytax-6,1,1-dien-13-yl (2R,3S)-3-(tert-butoxycarbonylamino)-3-(3-fluoro-2-pyridyl)-2-triisopropylsilyloxypropionate (compound 9).

The residue was dissolved in ethanol (17 L), and ammonium formate (0.41 kg) and 10% palladium-carbon (0.65 g, water content 50%) were added thereto and stirred at about 45° C. for about 1 hour. Then, ammonium formate (0.41 kg) was again added thereto, and stirred for 2 hours. The termination of the reaction was confirmed, palladium-carbon was removed through filtration, and the filtrate was concentrated to dryness under reduced pressure to obtain a residue of (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-triisopropylsilyloxypropionate (compound 10).

The residue was dissolved in ethyl acetate (13 L), and 1 mol/L tetrabutylammonium fluoride-tetrahydrofuran solution (1.3 L, 1.30 mol) was added thereto and stirred at room temperature for about 1 hour. The termination of the reaction was confirmed through HPLC, and then ethyl acetate and 4% sodium hydrogencarbonate were added thereto for extraction and liquid-liquid separation. The organic layer was washed with saturated saline water, and concentrated to dryness under reduced pressure. The residue was dissolved in acetone (15.2 L), then water (10.2 L) was added thereto, and thereafter a seed crystal was added thereto and stirred overnight. Next, with further stirring and with cooling with ice-cold water, this was cooled for about 7 hours, and then the crystal was taken out through filtration and dried under reduced pressure to obtain the entitled compound (compound 11, 543 g).

Compound 8: (1S,2S,3R,4S,5R,8R,9S,10R,13S)-4-Acetoxy-2-benzoyloxy-5,20-epoxy-1-hydroxy-9,10-[(1S)-2,3-dihydroxypropylidenedioxy]tax-6,11-dien-13-yl(2R,3S)-3-(tert-butoxycarbonylamino-3-(3-fluoro-2-pyridyl)-2-triisopropylsilyloxypropionate (8)

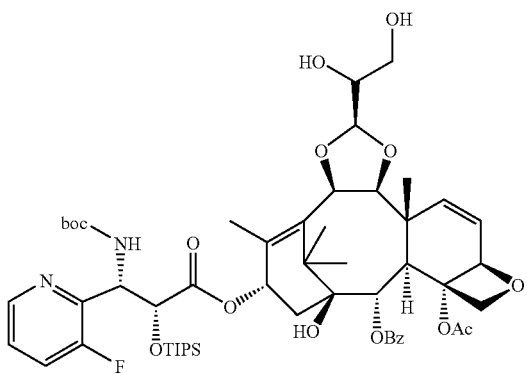

MS (FAB) m/z: 1039 [M+H]$^+$
HRMS (FAB) m/z: 1039.4967 calculated value as [M+H]$^+$ 1039.4999

Compound 9: (1S,2S,3R,4S,5R,8R,9S,10R,13S)-4-Acetoxy-2-benzoyloxy-9,10[(1S)-2-(dimethylamino)ethylidenedioxy]-5,20-epoxy-1-hydroxytax-6,11-dien-13-yl(2R,3S)-3-(tert-butoxycarbonylamino)-3-(3-fluoro-2-pyridyl)-2-triisopropylsilyloxypropionate (9)

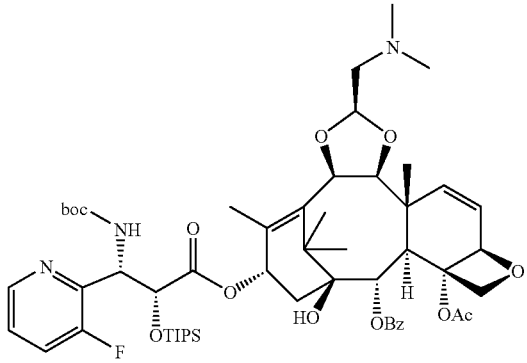

$^1$H-NMR (400 MHz, CDCl$_3$, TMS) δ: 0.87-0.92 (21H, m), 1.32 (3H, s), 1.38 (9H, s), 1.55 (3H, s), 1.57 (3H, s), 1.75 (3H, s), 2.39 (6H, s), 2.42-2.45 (2H, m), 2.51 (3H, s), 2.66 (1H, dd, J=5.1, 13.2 Hz), 2.74 (1H, dd, J=4.2, 13.2 Hz), 3.14 (1H, d, J=5.8 Hz), 4.01 (1H, d, J=7.9 Hz), 4.32 (2H, s), 4.90-4.94 (2H, m), 5.00 (1H, t, J=4.9 Hz), 5.15 (1H, d, J=7.9 Hz), 5.63 (1H, d, J=9.8 Hz), 5.69 (1H, dd, J=9.8, 4.4 Hz), 5.95 (1H, d, J=5.8 Hz), 6.07-6.13 (3H, m), 7.26-7.28 (1H, m), 7.41 (1H, t, J=9.2 Hz), 7.49 (2H, t, J=7.5 Hz), 7.59 (1H, t, J=7.5 Hz), 8.17 (2H, d, J=7.5 Hz), 8.40 (1H, d, J=4.4 Hz).

Compound 10: (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl(2R,3S)-3-(tert-butoxycarbonylamino)-3-(3-fluoro-2-pyridyl)-2-triisopropylsilyloxypropionate (10)

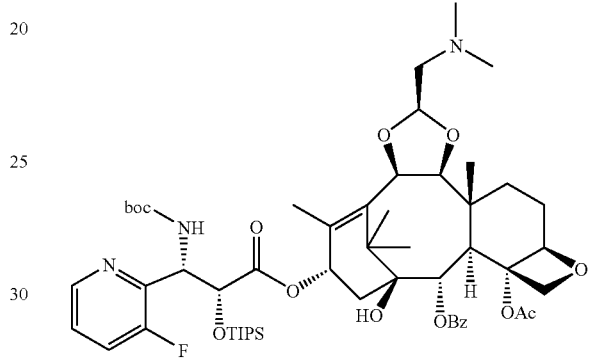

$^1$H-NMR (400 MHz, CDCl$_3$, TMS) δ: 0.83-0.93 (21H, m), 1.35 (3H, s), 1.38 (9H, s), 1.52 (3H, s), 1.56-2.07 (5H, m), 1.62 (3H, s), 1.81 (3H, s), 2.34-2.43 (2H, m), 2.38 (6H, s), 2.49 (3H, s), 2.66 (1H, dd, J=5.4, 13.2 Hz), 2.74 (1H, dd, J=3.4, 13.2 Hz), 2.98 (1H, d, J=5.4 Hz), 4.17 (1H, d, J=7.3 Hz), 4.22 (1H, d, J=7.8 Hz), 4.36 (1H, d, J=8.3 Hz), 4.96 (2H, s), 5.00 (1H, t, J=4.8 Hz), 5.22 (1H, d, J=7.3 Hz), 5.60 (1H, d, J=8.8 Hz), 5.98 (1H, d, J=4.9 Hz), 6.08-6.10 (2H, m), 7.26-7.28 (1H, m), 7.40 (1H, t, J=9.2 Hz), 7.48 (2H, t, J=7.5 Hz), 7.59 (1H, t, J=7.5 Hz), 8.16 (2H, d, J=7.5 Hz), 8.40 (1H, d, J=3.9 Hz).

Compound 11: (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl(2R,3S)-3-(tert-butoxycarbonylamino)-3-(3-fluoro-2-pyridyl)-2-hydroxypropionate (11)

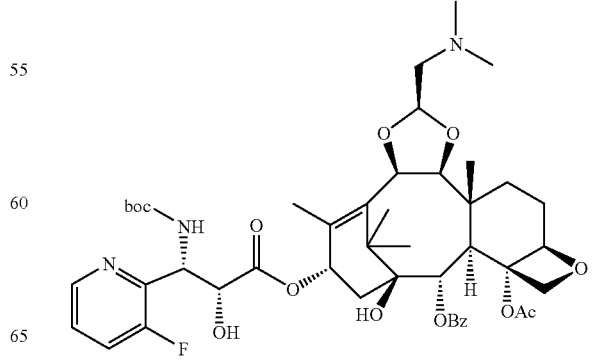

¹H-NMR (400 MHz, CDCl₃, TMS) δ: 1.29 (3H, s), 1.41 (9H, s), 1.49 (3H, s), 1.63 (3H, s), 1.79 (3H, s), 1.86-2.08 (5H, m), 2.32-2.38 (2H, m), 2.34 (3H, s), 2.38 (6H, s), 2.66 (1H, dd, J=5.4, 13.6 Hz), 2.75 (1H, dd, J=3.9, 13.6 Hz), 2.94 (1H, d, J=4.9 Hz), 4.14 (1H, d, J=6.9 Hz), 4.23 (1H, d, J=8.3 Hz), 4.33 (1H, d, J=8.3 Hz), 4.68 (1H, d, J=2.9 Hz), 4.92 (1H, s), 5.02 (1H, t, J=4.9 Hz), 5.25 (1H, d, J=6.8 Hz), 5.65 (1H, d, J=8.3 Hz), 6.00 (1H, d, J=4.9 Hz), 6.09 (1H, t, J=7.8 Hz), 6.21 (1H, d, J=8.3 Hz), 7.28-7.33 (1H, m), 7.43-7.49 (3H, m), 7.60 (1H, t, J=7.3 Hz), 8.14 (2H, d, J=7.3 Hz), 8.40 (1H, d, J=4.4 Hz).

Example 7

Production Method 2 for (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl(2R,3S)-3-(tert-butoxycarbonylamino)-3-(3-fluoro-2-pyridyl)-2-hydroxypropionate (compound 11)

Pyridine (450 mL) and water (25.9 mL) were added to (1S,2S,3R,4S,5R,8R,9S,10R,13S)-4-acetoxy-2-benzoyloxy-5,20-epoxy-1-hydroxy-9,10-[(1S)-2-propenylidenedioxy]tax-6,11-dien-13-yl(2R,3S)-3-(tert-butoxycarbonylamino-3-(3-fluoro-2-pyridyl)-2-triisopropylsilyloxypropionate (compound 7) (30.0 g, 29.8 mmol), and stirred at room temperature, and aqueous 4 N lithium hydroxide solution (1.49 mL, 5.96 mmol), aqueous 50 g/L potassium permanganate solution (122.6 mL, 38.8 mmol) were added thereto, and stirred for about 30 minutes. Ethyl acetate, aqueous 10% citric acid solution and saturated saline water were added to the reaction mixture for extraction and liquid-liquid separation. The organic layer was taken out, washed with a mixture of aqueous 10% citric acid solution and saturated saline water, and then with a mixture of aqueous 4% sodium hydrogencarbonate solution and saturated saline water, and thereafter concentrated under reduced pressure to obtain a residue of (1S,2S,3R,4S,5R,8R,9S,10R,13S)-4-acetoxy-2-benzoyloxy-5,20-epoxy-1-hydroxy-9,10-[(1S)-2,3-dihydroxypropylidenedioxy]tax-6,11-dien-13-yl(2R,3S)-3-(tert-butoxycarbonylamino-3-(3-fluoro-2-pyridyl)-2-triisopropylsilyloxypropionate (compound 8).

The residue was dissolved in acetonitrile (300 mL), and sodium periodate (12.8 g, 59.7 mmol) dissolved in pyridine (30 mL) and water (100 mL) was added thereto, and stirred at 40° C. for about 2 hours. After the termination of the reaction was confirmed, aqueous 20% sodium thiosulfate solution was added to it and stirred for a while, and then filtered through Celite, and the filtrate was concentrated under reduced pressure. The concentrated mixture was extracted with ethyl acetate, the organic layer was taken out, washed twice with a mixture of 2 N hydrochloric acid and saturated saline water, and then once with a mixture of 4% sodium hydrogencarbonate and saturated saline water. The organic layer was dried over magnesium sulfate, concentrated under reduced pressure, and tetrahydrofuran (300 mL), acetic acid (1.70 mL, 29.8 mmol) and 2 mol/L dimethylamine-methanol solution (22.4 mL, 44.8 mmol) were added to it, and stirred with cooling with ice-cold water. Sodium acetoxyborohydride (13.9 g, 65.6 mmol) was added to it, and stirred for about 2 hours. Then, the termination of the reaction was confirmed, and 4% sodium hydrogencarbonate and ethyl acetate were added to it for extraction and liquid-liquid separation. The organic layer was washed with a mixture of water and saturated saline water, dried over magnesium sulfate, and concentrated to dryness under reduced pressure to obtain a residue of (1S,2S,3R,4S,5R,8R,9S,10R,13S)-4-acetoxy-2-benzoyloxy-9,10[(1S)-2-(dimethylamino)ethylidenedioxy]-5,20-epoxy-1-hydroxytax-6,11-dien-13-yl(2R,3S)-3-(tert-butoxycarbonylamino-3-(3-fluoro-2-pyridyl)-2-triisopropylsilyloxypropionate (compound 9).

The residue was dissolved in ethanol (240 mL), activated charcoal (5.10 g) was added thereto, stirred at 40° C. for about 30 minutes, filtered, and ethanol (150 mL), water (83 mL), ammonium formate (9.5 g), and 10% palladium-carbon (15 g, water content 50%) were added to the filtrate, and stirred at about 45° C. for about 30 minutes. Ammonium formate (4.7 g) was again added to it, and stirred for about 30 minutes. The termination of the reaction was confirmed, then palladium-carbon was removed through filtration, and the filtrate was concentrated under reduced pressure. Ethyl acetate (300 mL) was added to the concentrated liquid for extraction and liquid-liquid separation. The organic layer was washed with aqueous 4% sodium hydrogencarbonate solution and then with saturated saline water. The organic layer was dried over magnesium sulfate, and concentrated to dryness under reduced pressure to obtain a residue of (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl(2R,3S)-3-(tert-butoxycarbonylamino)-3-(3-fluoro-2-pyridyl)-2-triisopropylsilyloxypropionate (compound 10).

The residue was dissolved in ethyl acetate (300 mL), and 1 mol/L tetrabutylammonium fluoride-tetrahydrofuran solution (30 mL, 30 mmol) was added to it and stirred at room temperature for about 1 hour. After the termination of the reaction was confirmed, a mixture of aqueous 4% sodium hydrogencarbonate solution and saturated saline water was added thereto for extraction and liquid-liquid separation. The organic layer was washed with saturated saline water, and concentrated to dryness under reduced pressure. The residue was dissolved in acetone (332 mL), and water (222 mL) was added thereto, and then a seed crystal was added thereto, and stirred overnight. Next, with further stirring and with cooling with ice-cold water, this was cooled for about 5 hours, and the crystal was taken out through filtration and dried under reduced pressure to obtain the entitled compound (compound 11, 15.2 g).

Example 8

Production Method 3 for (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl(2R,3S)-3-(tert-butoxycarbonylamino)-3-(3-fluoro-2-pyridyl)-2-hydroxypropionate (Compound 11

A concentrated residue of (3R,4S)-1-(tert-butoxycarbonyl)-4-(3-fluoro-2-pyridyl)-3-triisopropylsilyloxy-2-azetidinone (92.7 mmol) was dissolved in diisopropyl ether (410 mL), and 4-bromothiophenol (18.4 g, 97.3 mmol) and potassium carbonate (14.7 g) were added thereto and stirred at room temperature for about 30 minutes. The disappearance of (3R,4S)-1-(tert-butoxycarbonyl)-4-(3-fluoro-2-pyridyl)-3-triisopropylsilyloxy-2-azetidinone was confirmed, and water (290 mL) was added to it for liquid-liquid separation. The organic layer was separated, washed with saturated saline water (290 mL), and dried over magnesium sulfate. The insoluble matter was removed through filtration, and the filtrate was concentrated under reduced pressure to obtain a residue of S-(4-bromophenyl)(2R,3S)-3-[(tert-butoxycarbonyl)amino]-3-(3-fluoro-2-pyridinyl)-2-[(triisopropylsilyl)oxy]propanethioate.

On the other hand, dimethoxyethane (280 mL) was added to sodium hydride (7.41 g, content 60%, 185 mmol), and the system was purged with nitrogen gas. Then, with cooling with ice-cold water, (1S,2S,3R,4S,5R,8R,9S,10R,13S)-4-acetoxy-2-benzoyloxy-5,20-epoxy-1,13-dihydroxy-9,10-[(1S)-2-propenylidenedioxy]tax-6,11-diene (35.0 g, 61.8 mmol) dissolved in dimethoxyethane (245 mL) was dropwise added to it. Next, the above reaction residue, S-(4-bromophenyl)(2R,3S)-3-[(tert-butoxycarbonyl)amino]-3-(3-fluoro-2-pyridinyl)-2-[(triisopropylsilyl)oxy]propanethioate dissolved in dimethoxyethane (175 mL) was dropwise added to it, taking 15 minutes. Then, cooling with ice-cold water was stopped, and this was stirred for about 2 hours. The termination of the reaction was confirmed, and then the reaction liquid was added to a mixture of aqueous 4% sodium hydrogencarbonate solution (315 mL) and ethyl acetate (350 mL) with cooling with ice-cold water, and saturated saline water (175 mL) was added thereto for extraction and liquid-liquid separation. The organic layer was taken out, washed with a mixture of water (350 mL) and saturated saline water (210 mL), and then with saturated saline water (315 mL), and thereafter this was concentrated under reduced pressure. Ethanol (805 mL) was added to the concentrated residue, dissolved under heat at 50° C., and then a seed crystal was added to it, and stirred overnight at room temperature. Next, with cooling with ice-cold water, this was further kept stirred for 3 hours, and the precipitated crystal was taken out through filtration. The crystal was dried under reduced pressure, and formed into slurry with a (1/1) mixture (690 mL) of cyclohexane/n-heptane, and taken out through filtration and dried at 50° C. under reduced pressure to obtain (1S,2S,3R,4S,5R, 8R,9S,10R,13S)-4-acetoxy-2-benzoyloxy-5,20-epoxy-1-hydroxy-9,10-[(1S)-2-propenylidenedioxy]tax-6,11-dien-13-yl(2R,3S)-3-(tert-butoxycarbonylamino-3-(3-fluoro-2-pyridyl)-2-triisopropylsilyloxypropionate (52.2 g, 52.2 mmol).

40.0 g (39.8 mmol) of the above product was dissolved in pyridine (600 mL), then water (94 mL) was added thereto, and aqueous 50 g/L potassium permanganate solution (164 mL, 51.7 mmol) was added thereto at 35° C., and stirred for about 30 minutes. Ethyl acetate (600 mL), aqueous 10% citric acid solution (200 mL) and saturated saline water (120 mL) were added to the reaction liquid for extraction and liquid-liquid separation. The organic layer was taken out, washed with a mixture of aqueous 10% citric acid solution (120 mL) and saturated saline water (120 mL), and then with a mixture of aqueous 4% sodium hydrogencarbonate solution (200 mL) and saturated saline water (120 mL), and thereafter concentrated under reduced pressure to obtain a residue of (1S,2S, 3R,4S,5R,8R,9S,10R,13S)-4-acetoxy-2-benzoyloxy-5,20-epoxy-1-hydroxy-9,10-[(1S)-2,3-dihydroxypropylidenedioxy]tax-6,11-dien-13-yl(2R,3S)-3-(tert-butoxycarbonylamino-3-(3-fluoro-2-pyridyl)-2-triisopropylsilyloxypropionate.

The residue was dissolved in acetonitrile (280 mL), and activated charcoal (6 g) was added thereto and stirred at room temperature for about 30 minutes. The insoluble matter was removed through filtration, the filtrate was washed with acetonitrile (120 mL), then sodium periodate (17.0 g, 79.6 mmol) dissolved in pyridine (40 mL) and water (130 mL) was added to it, and stirred overnight at room temperature. After the termination of the reaction was confirmed, aqueous 20% sodium thiosulfate solution was added to it, and stirred for a while. Then, this was filtered through Celite, and the filtrate was concentrated under reduced pressure. Ethyl acetate (400 mL) and saturated saline water (80 mL) were added to the concentrated liquid for extraction, the organic layer was taken out, and washed twice with a mixture of 2 N hydrochloric acid (80 mL) and saturated saline water (80 mL), and then once with a mixture of 4% sodium hydrogencarbonate (160 mL) and saturated saline water (160 mL). The organic layer was dried over magnesium sulfate, then concentrated under reduced pressure to about 400 mL. Dimethylamine hydrochloride (4.9 g, 59.7 mmol) and sodium acetate (4.9 g, 59.7 mmol) were added to it, and stirred with cooling with ice-cold water. After about 20 minutes, sodium acetoxyborohydride (12.6 g, 59.7 mmol) was added to it, and stirred for about 1.5 hours. After the termination of the reaction was confirmed, aqueous 15% potassium hydrogencarbonate solution (280 mL) and saturated saline water (120 mL) were added to it for extraction and liquid-liquid separation. The organic layer was washed with a mixture of water (200 mL) and saturated saline water (120 mL), and concentrated under reduced pressure to obtain a residue of (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-6,11-dien-13-yl (2R,3S)-3-(tert-butoxycarbonylamino)-3-(3-fluoro-2-pyridyl)-2-triisopropylsilyloxypropionate.

The residue was dissolved in ethanol (320 mL), and activated charcoal (6 g) was added to it and stirred at room temperature. The insoluble matter was removed through filtration, the filtrate was washed with ethanol (200 mL), and water (110 mL), ammonium formate (12.5 g) and 10% palladium-carbon (20 g, water content 50%) were added to it, and stirred at about 45° C. for about 1.5 hours. After the termination of the reaction was confirmed, palladium-carbon was removed through filtration, and the filtrate was concentrated under reduced pressure. The residue was dissolved in ethyl acetate (600 mL), and a mixture of 4% sodium hydrogencarbonate (280 mL) and saturated saline water (120 mL) was added thereto for extraction and liquid-liquid separation. The organic layer was washed with saturated saline water (280 mL), and dried over magnesium sulfate, and then concentrated under reduced pressure to obtain a residue of (1S, 2S,3R,4S,5R,8R,9S,10R,13S)-4-acetoxy-2-benzoyloxy-9, 10-[(1S)-2-(dimethylamino)ethylidenedioxy]-5,20-epoxy-1-hydroxytax-11-en-13-yl(2R,3S)-3-(tert-butoxycarbonylamino)-3-(3-fluoro-2-pyridyl)-2-triisopropylsilyloxypropionate.

The residue was dissolved in ethyl acetate (600 mL), and with cooling with ice-cold water, 1 mol/L tetrabutylammonium fluoride-tetrahydrofuran solution (40 mL, 40.0 mmol) was added to it and stirred for about 1 hour. After the termination of the reaction was confirmed, a mixture of aqueous 4% sodium hydrogencarbonate solution (400 mL) and saturated saline water (200 mL) was added to it for extraction and liquid-liquid separation. The organic layer was washed with saturated saline water (400 mL), and concentrated under reduced pressure. The residue was dissolved in acetone (290 mL), activated charcoal (5.46 g) was added to it, and stirred at room temperature for about 30 minutes. The insoluble matter was removed through filtration, the filtrate was washed with acetone (146 mL), and water (290 mL) was added to the filtrate with stirring. Then, this was stirred overnight. With that, this was kept stirred and cooled with ice-cold water, and after cooled for about 5 hours, the formed crystal was taken out through filtration and dried under reduced pressure to obtain the entitled compound (20.7 g).

Example 9

Comparison with Conventional Method

A case of obtaining the compound 11 from the compound 7 according to the method described in Example 6 of the invention was compared with a case of obtaining the compound 11 from the compound 7 according to the method described in JP-A-2002-332287 where osmium tetroxide is used for the dihydroxylation of the compound 7, in point of the yield of the product. The result is shown in the following Table. Similarly, in the method of Example 7 or 8, the yield of the product was higher than that in the conventional method.

TABLE 5

| | | Compound 11 | |
| --- | --- | --- | --- |
| | Oxidizing Agent | Yield of Crude Crystal (%) | Yield of Purified Crystal (%) |
| Conventional Method | osmium tetroxide | 39 | 29 |
| Method of the Invention | potassium permanganate | 47 | 40 |

As compared with that in the conventional method, the yield of both the crude crystal and the purified crystal was increased in the method of the invention.

While the invention has been described in detail and with reference to specific embodiments thereof, it will be apparent to one skilled in the art that various changes and modifications can be made therein without departing from the spirit and scope thereof.

This application is based on Japanese Patent Application (No. 2004-136359) filed Apr. 30, 2004, the contents thereof being hereby incorporated by reference.

INDUSTRIAL APPLICABILITY

The taxan derivatives obtained according to the production method of the invention are useful as orally-administrable antitumor compounds.

The invention claimed is:

1. A method for producing a compound of the following general formula (11) or its salt, which comprises reacting a compound of the following general formula (14):

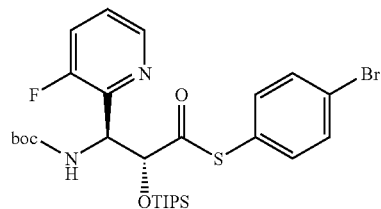

(14)

(in formula (14), boc means a tert-butoxycarbonyl group; TIPS means a triisopropylsilyl group), with a compound of the following general formula (19):

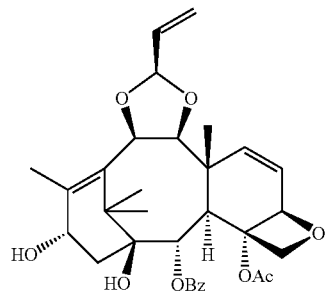

(19)

(in formula (19), Ac means an acetyl group; and Bz means a benzoyl group)

to produce a compound of the following general formula (7):

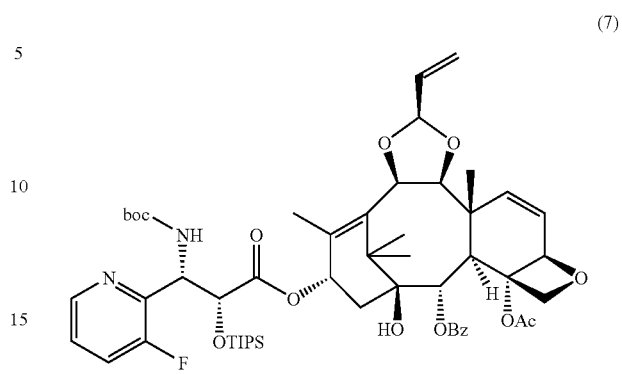

(7)

(in formula (7), boc, Ac, Bz and TIPS have the same meanings as above), then reacting the compound of formula (7) with potassium permanganate in aqueous pyridine to obtain a compound of the following general formula (8):

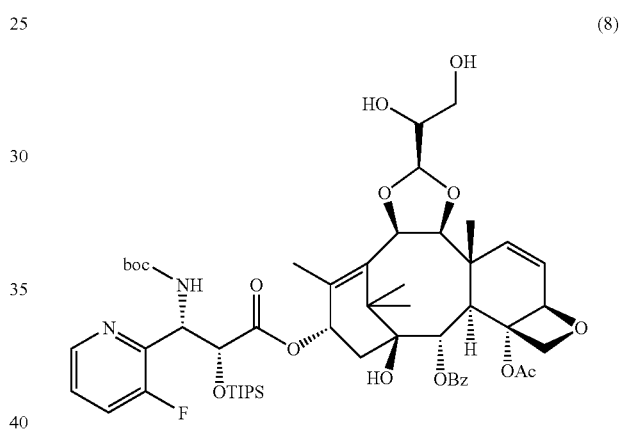

(8)

(in formula (8), boc, Ac, Bz and TIPS have the same meanings as above), reacting the compound of formula (8) with an alkali metal periodate, and then with sodium acetoxyborohydride in the presence of acetic acid and dimethylamine to obtain a compound of the following general formula (9):

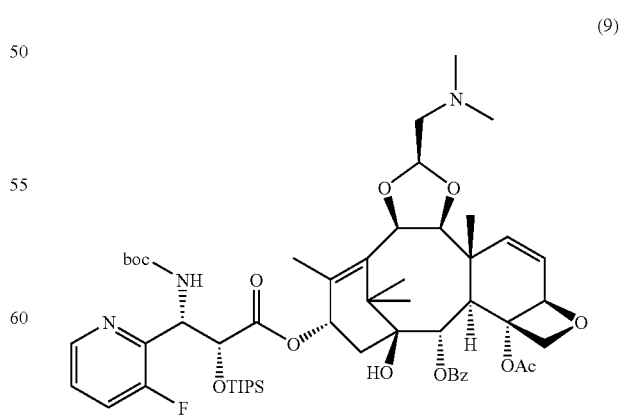

(9)

(in formula (9), boc, Ac, Bz and TIPS have the same meanings as above), and then reacting the compound of formula (9)

with a palladium-carbon catalyst in the presence of hydrogen gas to thereby reduce the compound of formula (9) into a compound of the following general formula (10):

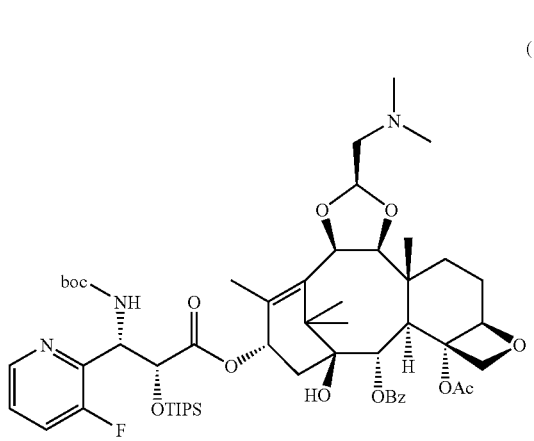

(10)

(in formula (10), boc, Ac, Bz and TIPS have the same meanings as above), and thereafter reacting the compound of formula (10) with a fluoroammonium salt to produce a compound of the following general formula (11) or its salt:

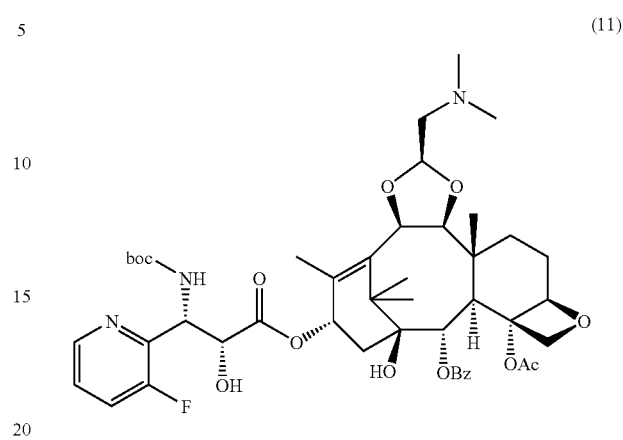

(11)

(in formula (11), boc, Ac and Bz have the same meanings as above).

* * * * *